(12) United States Patent
Van Berkel et al.

(10) Patent No.: US 8,519,330 B2
(45) Date of Patent: Aug. 27, 2013

(54) SYSTEMS AND METHODS FOR LASER ASSISTED SAMPLE TRANSFER TO SOLUTION FOR CHEMICAL ANALYSIS

(75) Inventors: Gary J. Van Berkel, Oak Ridge, TN (US); Vilmos Kertesz, Koroncó (HU); Olga S. Ovchinnikova, Knoxville, TN (US)

(73) Assignees: UT-Battelle, LLC, Knoxville, TN (US); University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/152,836

(22) Filed: Jun. 3, 2011

(65) Prior Publication Data
US 2012/0079894 A1 Apr. 5, 2012

Related U.S. Application Data

(63) Continuation-in-part of application No. 12/896,018, filed on Oct. 1, 2010.

(51) Int. Cl.
*G01N 1/22* (2006.01)
(52) U.S. Cl.
USPC .......................... 250/288; 250/423 R; 850/63
(58) Field of Classification Search
USPC ............... 250/281, 282, 288, 423 R; 850/33, 850/62, 63
See application file for complete search history.

(56) References Cited

U.S. PATENT DOCUMENTS

| | | | |
|---|---|---|---|
| 4,726,487 A | 2/1988 | Mitri | |
| 4,745,809 A | 5/1988 | Collins et al. | |
| 4,865,199 A | 9/1989 | Zimmer | |
| 5,205,473 A | 4/1993 | Coffin, Sr. | |
| 5,271,798 A | 12/1993 | Sandhu et al. | |
| 5,783,938 A | 7/1998 | Munson et al. | |
| 6,140,639 A | 10/2000 | Gusev et al. | |
| 6,290,863 B1 | 9/2001 | Morgan et al. | |
| 6,409,832 B2 | 6/2002 | Weigl et al. | |

(Continued)

FOREIGN PATENT DOCUMENTS

| | | |
|---|---|---|
| DE | 4200497 | 7/1993 |
| DE | 4207074 | 9/1993 |

(Continued)

OTHER PUBLICATIONS

Meister, A., et al. "Nanodispenser for attoliter volume deposition using atomic force microscopy probes modified by focused-ion-beam-milling" Appl. Phys. Lett. 85, 6260 (2004).*

(Continued)

*Primary Examiner* — David A Vanore
*Assistant Examiner* — Wyatt Stoffa
(74) *Attorney, Agent, or Firm* — Novak Druce Connolly Bove + LLP

(57) ABSTRACT

Systems and methods are described for laser ablation of an analyte from a specimen and capturing of the analyte in a dispensed solvent to form a testing solution. A solvent dispensing and extraction system can form a liquid microjunction with the specimen. The solvent dispensing and extraction system can include a surface sampling probe. The laser beam can be directed through the surface sampling probe. The surface sampling probe can also serve as an atomic force microscopy probe. The surface sampling probe can form a seal with the specimen. The testing solution including the analyte can then be analyzed using an analytical instrument or undergo further processing.

2 Claims, 27 Drawing Sheets

(56) References Cited

U.S. PATENT DOCUMENTS

| | | | |
|---|---|---|---|
| 6,478,238 B1* | 11/2002 | Wachs et al. | 239/338 |
| 6,803,566 B2* | 10/2004 | Van Berkel | 250/288 |
| 6,864,480 B2 | 3/2005 | Staats | |
| 7,270,948 B2 | 9/2007 | Demirev | |
| 7,445,907 B2 | 11/2008 | Everett et al. | |
| 7,525,105 B2 | 4/2009 | Kovtoun | |
| 7,718,958 B2 | 5/2010 | Shiea et al. | |
| 7,762,638 B2 | 7/2010 | Cruchon-Dupeyrat et al. | |
| 8,067,730 B2* | 11/2011 | Vertes et al. | 250/288 |
| 2002/0168778 A1 | 11/2002 | Andrien et al. | |
| 2003/0193020 A1* | 10/2003 | Van Berkel | 250/288 |
| 2004/0023410 A1 | 2/2004 | Stacey | |
| 2004/0226464 A1* | 11/2004 | Mirkin et al. | 101/483 |
| 2005/0082475 A1* | 4/2005 | Doan | 250/288 |
| 2005/0087122 A1 | 4/2005 | Ismagliov et al. | |
| 2005/0116161 A1 | 6/2005 | Hafeman et al. | |
| 2005/0178959 A1 | 8/2005 | Lopez-Avila et al. | |
| 2005/0276937 A1 | 12/2005 | Kosth | |
| 2007/0046934 A1 | 3/2007 | Roy | |
| 2007/0138384 A1 | 6/2007 | Keiser | |
| 2007/0224697 A1 | 9/2007 | Park | |
| 2007/0259445 A1 | 11/2007 | Cerda | |
| 2007/0295902 A1 | 12/2007 | Shea et al. | |
| 2008/0128614 A1* | 6/2008 | Nikolaev et al. | 250/288 |
| 2008/0131949 A1 | 6/2008 | Bortolin et al. | |
| 2008/0230387 A1 | 9/2008 | McBride et al. | |
| 2008/0272294 A1 | 11/2008 | Kovtoun | |
| 2008/0308722 A1 | 12/2008 | Shiea | |
| 2009/0000364 A1 | 1/2009 | Yu | |
| 2009/0053689 A1 | 2/2009 | Oviso et al. | |
| 2009/0121124 A1 | 5/2009 | Schneider | |
| 2009/0253210 A1 | 10/2009 | Kobold et al. | |
| 2009/0263440 A1 | 10/2009 | Kendall | |
| 2010/0038529 A1 | 2/2010 | Sato et al. | |
| 2010/0224013 A1 | 9/2010 | Van Berkel et al. | |
| 2011/0100091 A1 | 5/2011 | Harrup et al. | |
| 2011/0133077 A1* | 6/2011 | Henion et al. | 250/288 |
| 2011/0259205 A1 | 10/2011 | Delorme | |
| 2012/0074306 A1* | 3/2012 | Jesse et al. | 250/288 |
| 2012/0083045 A1* | 4/2012 | Van Berkel et al. | 250/288 |
| 2012/0119079 A1 | 5/2012 | Ouyang et al. | |

FOREIGN PATENT DOCUMENTS

| | | |
|---|---|---|
| DE | 102004048380 | 4/2006 |
| DE | 102006056929 | 6/2008 |
| EP | 1252366 | 10/2002 |
| GB | 1272409 | 4/1972 |
| GB | 1451599 | 10/1976 |
| JP | 07159293 | 6/1995 |
| JP | 10148605 | 6/1998 |
| JP | 2003035671 | 2/2003 |
| JP | 2006059641 | 3/2006 |

OTHER PUBLICATIONS

Becker et al., "Evidence of Near-Field Laser Ablation Inductively Coupled Plasma Mass Spectrometry (NF-LA-ICP-MS) at Nanometre Scale for Elemental and Isotopic Analysis on Gels and Biological Samples," Journal of Analytical Atomic Spectrometry, 2006, p. 19-25, vol. 21, The Royal Society of Chemistry.

Bohn et al., "Field Enhancement in Apertureless Near-Field Scanning Optical Microscopy," J. Opt. Soc. Am. A/vol. 18, No. 12/Dec. 2001, p. 2998-3006, Optical Society of America.

Chapter 2 "Liquid-Phase Pulsed Laser Ablation."

Chen et al., "The Irradiation Effect of a Nd-YAG Pulsed Laser on the $CeO_2$ Target in the Liquid," Materials Letters, 2004, p. 337-341. vol. 58, Elsevier.

De Serio, M. et al. "Looking at the nanoscale: scanning near-field optical microscopy." Trends in Analytical Chemistry, vol. 22, No. 2, 2003.

Douglas et al., "Laser Ablation of a Sample in Liquid—LASIL," J. Anal. At. Spectrom., 2011, The Royal Society of Chemistry.

Dunn, Robert C., "Near-Field Scanning Optical Microscopy," Chem. Rev., 1999, p. 2891-2927, vol. 99.

Leung, et al., "Transmission Studies of Explosive Vaporization of a Transparent Liquid Film on an Opaque Solid Surface Induced by Excimer-Laser-Pulsed Irradiation," J. Appl. Phy., 1992, p. 2256-2263, vol. 72 No. 6.

M. Meunier et al., "Laser Processing Laboratory. Colloidal metal nanoparticles synthesized by femtosecond laser ablation in liquids." http://LPL.phys.polymtl.ca. Retrieved Mar. 8-10, 2005.

Muravitskaya et al., "Laser Ablation in Liquids as a New Technique of Sampling in Elemental Analysis of Solid Materials," Spectrochimica Acta Part B, 2009, p. 119-125, vol. 64, Elsevier B.V.

Novotny et al., "Near-Field Optical Microscopy and Spectroscopy with Pointed Probes," Annu. Rev. Phys. Chem., 2006, p. 303-331, vol. 57, Annual Reviews.

Reedy, M. Praveen, "Solid Dispersions" last visited Oct. 19, 2011 and presented at http://www.authorstream.com/Presentation/robin__vinnu-623593-solid-dispersions/(video).

Schmid, Thomas et al., "Methods for Modecular Nanoanalysis." CHIMIA 2006, 60, No, 11, pp. 783-788.

Schmidtz et al., "Towards Nanoscale Molecular Analysis at Atmospheric Pressure by A Near-Field Laser Ablation Ion Trap/Time-of-Flight Mass Spectrometer," Analytical Chemistry, 2008, p. 6537-6544, vol. 80 No. 17.

Stöckle et al., "Nanoscale Atmospheric Pressure Laser Ablation-Mass Spectrometry," Analytical Chemistry, 2001, p. 1399-1402, vol. 73-7, American Chemical Society.

Tsuji et al., "Microsecond-Resolved Imaging of Laser Ablation at Solid-Liquid Interface: Investigation of Formation Process of Nano-Size Metal Colloids," Applied Surface Science, 2004, p. 365-371, vol. 229, Elsevier B.V.

Yang, G.W., "Laser Ablation in Liquids: Applications in the Synthesis of Nanocrystals," Progress in Materials Science, 2007, p. 648-698, vol. 52, Elsevier.

Yasuo Lida, et al. "Laser ablation in a liquid Medium as a Technique for Solid Sampling." Journal of Analytical Atomic Spectrometry, Oct. 1991, vol. 6. pp. 541-544.

Yasushi Inouye., "Apertureless Metallic Probes for Near-Field Microscopy." Near-Field Optics and Surface Plasmon Polaritons, Topics Appl. Phys. 81, 29-48 (2001).

Yavas et al., "Optical Reflectance and Scattering Studies of Nucleation and Growth of Bubbles at a Liquid-Solid Interface Induced by Pulsed Laser Heating," Physical Review Letters. 1993, p. 1830-1833, vol. 70 No. 12, The American Physical Society.

Yavas, O. et al., "Bubble nucleation and pressure generation during laser cleaning surfaces," Appl. Phys. A 64, 331-339 (1997).

Zeisel et al., "Pulsed Laser-Induced Desorption and Optical Imaging on a Nanometer Scale With Scanning Near-Field Microscopy Using Chemically Etched Fiber Tips," Appl. Phys. Letter 1996, p. 2491-2, vol. 68 No. 18, Amer. Inst. of Physics.

Zijie Yan, et al. "Hollow nanoparticle generation on laser-induced cavitation bubbles via bubble interface pinning." Applied Physical Letters, 2010, p. 124106-1-3, vol. 97, Amer. Inst. of Physics.

Zoriy et al., "Possibility of Nano-Local Element Analysis by Near-Field Laser Ablation Inductively Coupled Plasma Mass Spectrometry (LA-ICP-MS): New Experimental Arrangement and First Application," International Journal of Mass Spectrometry, 2008, p. 151-155, vol. 273, Elsevier B.V.

International Search Report mailed Jan. 12, 2011. In corresponding PCT patent application No. PCTI US2011/053799.

International Search Report mailed Mar. 12, 2012. In corresponding PCT patent application No. PCTI US2011/054622.

International Search report mailed Dec. 1, 2011. In corresponding PCT patent application No. PCTI US2011/035604.

Eskin, Just a Day at the Beach, Jun. 2, 2002, Chicago Tribune.

Final Office Action issued on Jan. 17, 2013 in U.S. Appl. No. 13/102,606. (23 pages).

* cited by examiner

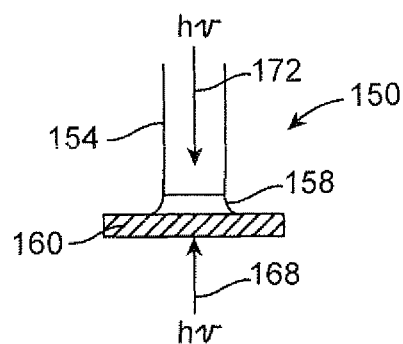
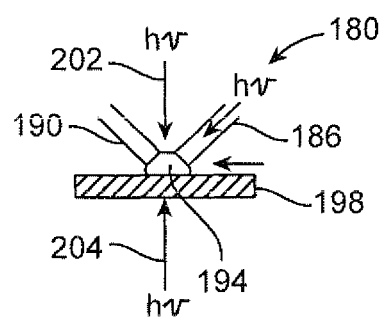
FIG. 17   FIG. 18
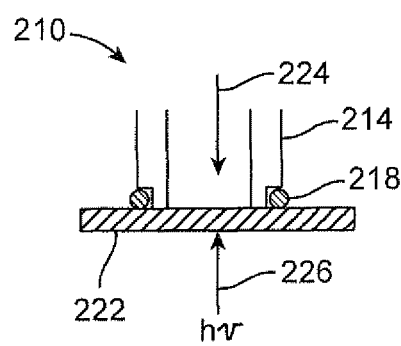
FIG. 19

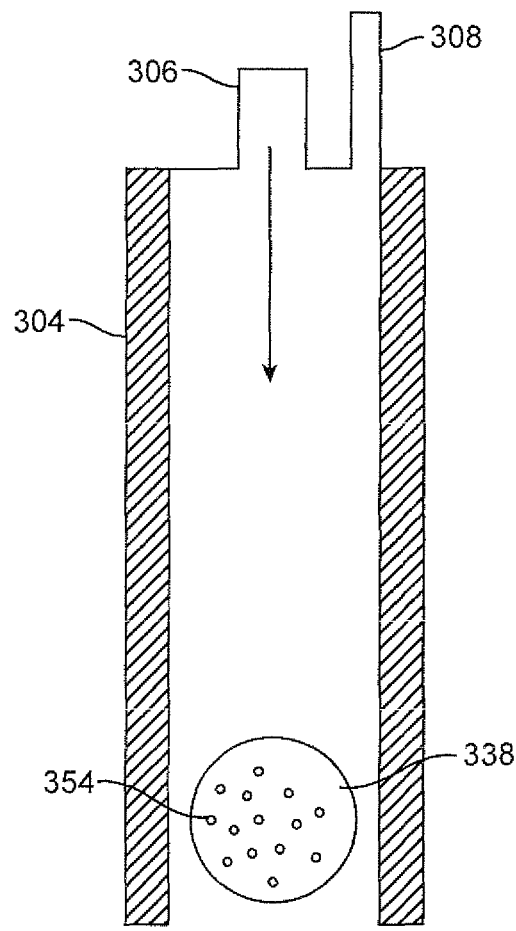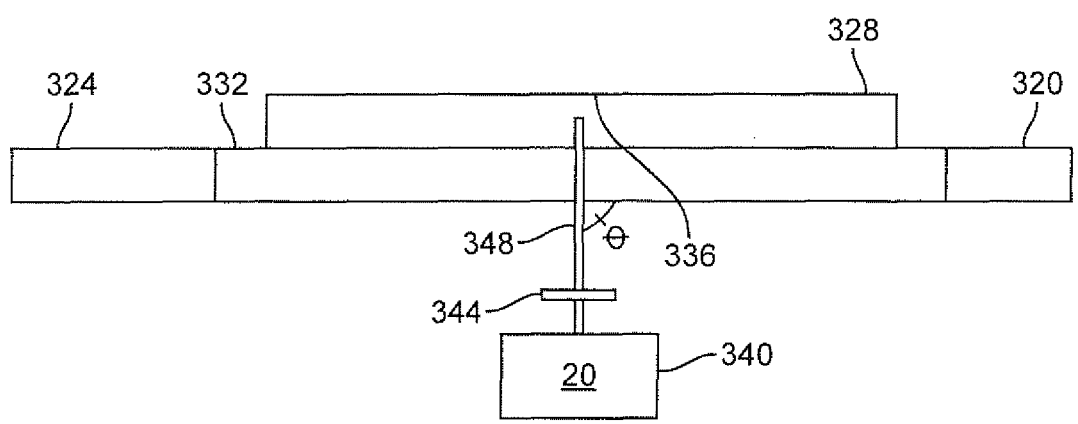
FIG. 27C

SYSTEMS AND METHODS FOR LASER ASSISTED SAMPLE TRANSFER TO SOLUTION FOR CHEMICAL ANALYSIS

CROSS REFERENCE TO RELATED APPLICATION

This application is a continuation-in-part of pending U.S. patent application Ser. No. 12/896,018 filed Oct. 1, 2010, the disclosure of which is incorporated fully by reference.

STATEMENT REGARDING FEDERALLY SPONSORED RESEARCH

This invention was made with government support under Contract No. DE-AC05-00OR22725 awarded by the U.S. Department of Energy. The government has certain rights in this invention.

FIELD OF THE INVENTION

This invention is drawn to systems and methods for surface sampling in general, and for laser assisted sample transfer to solution for analysis.

BACKGROUND OF THE INVENTION

Advances in analytical technology have pushed the limits of human understanding of chemical and physical phenomena. New tools create the opportunity for the new discoveries. Currently available techniques, such as laser desorption techniques, allow analysis of the chemical composition of surfaces at the micron level. However, conventional laser desorption techniques can be limited in their ability to desorb and ionize analytes present at the surface being analyzed. Thus, there is room for improvement in surface extraction technology.

Electrospray is an alternative to Matrix-assisted laser desorption/ionization (MALDI). Electrospray generally involves flowing a sample liquid into an electrospray ion source comprising a small tube or capillary which is maintained at a high voltage, in absolute value terms, with respect to a nearby surface. The nearby (e.g. 1 cm) surface is commonly referred to as the counter electrode. Conventional ES systems for mass spectrometry apply high voltage (relative to a ground reference) to the emitter electrode while holding the counter electrode at a lower, near ground reference voltage. For the positive ion mode of operation, the voltage on the emitter is high positive, while for negative ion mode the emitter voltage is high negative.

The liquid introduced into the tube or capillary is dispersed and emitted as line electrically charged droplets (plume) by the applied electrical field generated between the tube or capillary which is held at high voltage, referred to as the working electrode, and the nearby surface. In a typical ES-MS process, a solution containing analytes of interest is directed to the ES emitter which is held at high voltage, resulting in a charged solvent droplet spray or plume. The droplets drift towards the counter electrode under the influence of the electric field. As the droplets travel, gas-phase ions are liberated from the droplets. This process produces a quasi-continuous steady-state current with the charged droplets and ions constituting the current and completing the series circuit. Electrospray (ES) is a method of producing highly charged droplets and gas phase ions. A particularly useful application for electrospray is the production of gas phase ions from analytes in liquid solutions delivered by methods such as high pressure liquid chromatography, capillary electrophoresis or capillary electrochromatography to a system for detection and analysis, such as a mass spectrometer (MS). The electrospray process generally includes flowing an analyte liquid into an electrospray ion source comprising a small tube or capillary which is maintained at a high voltage in absolute value terms, with respect to a nearby surface. The small tube or capillary functions as an emitter electrode. In a typical ES-MS system, a solution containing analytes of interest is pumped through the emitter electrode and sprayed towards the remotely located orifice plate of the mass spectrometer. In this arrangement, the orifice plate functions as the counter electrode. Under the influence of the electric field between the emitter electrode and the orifice plate, ions in solution that are of the same polarity as the voltage applied to the ES capillary buildup an excess charge at the surface of the liquid exiting the emitter until a point is reached where the Coulombic forces are sufficient to overcome the surface tension of the liquid. At this point, droplets enriched in ions of this polarity are emitted from the capillary and drift toward the counter electrode. This process produces a quasi-continuous steady-state electrical current. Several methods for conducting surface sampling for electrospray mass spectrometry analysis, as well as other kinds of analysis, have been developed. Some such systems and methods are shown in U.S. Patents and Publications Nos. U.S. Pat. No. 6,803,566; U.S. Pat. No. 7,295,026, US 2010/0002905, and US 2010/0224013. The disclosure of these patents and publications is hereby incorporated fully by reference.

SUMMARY OF THE INVENTION

A method and system for laser assisted transfer of an analyte to a solution for analyzing the analyte is described. The system can include a specimen stage having a desorption region that is transparent to a radiation wavelength (λ); a sampling probe for suspending a solvent above the specimen stage; and a laser source for emitting a laser beam centered at the radiation wavelength (λ) toward the specimen stage. The laser source and the sampling probe can be on opposite sides of a primary surface of the specimen stage, i.e., in a transmission geometry.

The system can also include an analytical instrument for determining a chemical composition of an analyte in a testing solution comprising the solvent. The solvent can be in fluid communication with the analytical instrument. The analytical instrument can be a mass spectrometer, an ionization source, a separation method, or a combination thereof.

The system can also include a stepper mechanism configured to sequentially direct the laser beam at a plurality of target sites of a specimen supported by the specimen stage. The stepper mechanism can also be configured to provide relative motion between the specimen stage and the sampling probe.

The system can also include a testing device, which can be an analytical instrument or a device for processing the sample prior to evaluation with an analytical instrument. The stepper mechanism can be configured (i) to sequentially position the sampling probe to capture an analyte that is laser desorbed from each of a plurality of target sites with a suspended solvent to form a testing solution and (ii) to discharge the testing solution to the testing device. The testing solution is discharged from a distal end of said sampling probe.

The sampling probe can be a dual capillary sampling probe. For example, the sampling probe can include an outer capillary tube, and an inner capillary tube disposed co-axially within the outer capillary tube, where the inner and outer capillary tubes define a solvent capillary and a sampling capillary in fluid communication with one another at a distal end of the probe.

The invention also includes a system for extracting an analyte from a specimen that includes a specimen stage; a sampling probe configured to suspend a solvent to form an uninterrupted meniscus above said specimen stage; a laser source for emitting a laser beam centered at a radiation wavelength ($\lambda$) toward said specimen stage; and a stepper mechanism. The stepper mechanism can be configured to provide relative motion between the laser source and the specimen stage. The laser source and the sampling probe can both be on a primary surface side of the specimen stage. Alternately, the laser source and the sampling probe can be on opposite sides of a primary surface of the specimen stage.

A method of extracting an analyte from a specimen is also described. The method can include providing a specimen supported by a desorption region of a specimen stage; desorbing analyte from a target site of a specimen with a laser beam centered at a radiation wavelength ($\lambda$); and capturing the desorbed analyte with a suspended solvent to form a testing solution. The desorption region can be transparent to the radiation wavelength ($\lambda$), and both the specimen and the laser source emitting the laser beam can be on opposite sides of a primary surface of the specimen stage. The method can also include a step of analyzing a chemical composition of the desorbed analyte. Finally, the desorbing, capturing and analyzing steps can be repeated for each of a plurality of target sites of the specimen.

The invention also includes a method of analyzing a chemical composition of a specimen that includes desorbing an analyte from a target site of a specimen with a laser beam centered at a radiation wavelength ($\lambda$); capturing the desorbed analyte with a solvent suspended in the form of an uninterrupted meniscus above the specimen to form a testing solution; dispensing the testing solution to a testing device; automatically repositioning the specimen, the laser beam, or both; and repeating the desorbing, capturing and dispensing steps for a second target site of the specimen. The method can also include analyzing a chemical composition of the desorbed analyte. For example, the dispensing step can be into an analytical device.

A system for performing analysis of at least one analyte present in a solid sample, can include a laser source for emitting a laser beam toward a specimen on a specimen stage to generate ablated analyte; a solvent dispensing and extraction system, the solvent dispensing and extraction system dispensing a solvent adjacent to a surface of the sample such that at least a portion of the ablated analyte can be dissolved in the solvent, where the solvent dispensing and extraction system has structure for extracting the analyte-containing solvent for analysis.

The solvent dispensing and extraction system can position the solvent a distance away from the surface of the sample. The solvent dispensing and extraction system can form a liquid microjunction between the solvent dispensing and extraction system and a surface of the specimen. The solvent dispensing and extraction system can include a sampling probe for dispensing the solvent. The sampling probe when dispensing solvent can form a liquid microjunction with the specimen. The sampling probe can form a seal with a surface of the specimen. The laser can direct the laser beam through the sampling probe to the specimen. The sampling probe can be an atomic force microscopy probe. The laser beam can be emitted through the atomic force microscopy probe. The sampling probe can have a concentric solvent dispensing conduit and a solvent extraction conduit.

The solvent dispensing and extraction system can include a solvent dispensing probe and a solvent extraction conduit, an outlet of the solvent dispensing probe being separated by a distance from the inlet of the solvent extraction conduit. At least one of the solvent dispensing probe and the solvent extraction conduit can form a liquid microjunction with the specimen surface. The solvent dispensing and extraction system can deposit a quantity of solvent onto the specimen, stop the flow of solvent to the specimen, and after a predetermined time remove a portion of the solvent from the specimen. The laser can be on an opposite side of the specimen stage from the solvent dispensing and extraction system, and the specimen stage can be transmissive to the laser beam.

The system can include a stepper mechanism configured to sequentially direct the laser beam at a plurality of target sites of a specimen supported by the specimen stage. The stepper mechanism can be further configured to provide relative motion between the specimen stage and the sampling probe. The stepper mechanism can be configured (i) to sequentially position the sampling probe to capture an analyte that is laser ablated from each of a plurality of target sites with a suspended solvent to form a testing solution and (ii) to discharge the testing solution to the testing device. A controller can be provided, wherein the stepper mechanism is communicatively coupled to the controller, the controller being configured for actuating the stepper to sequentially direct the laser beam at plurality of target sites of a specimen supported by the specimen stage.

The system can include a focusing lens between the laser source and the specimen stage. The system can include an analytical instrument for determining a chemical composition of an analyte in a testing solution comprising the solvent. The extracted solvent can be in fluid communication with the analytical instrument. The analytical instrument can be a mass spectrometer, an ionization source, a separation method, or a combination thereof. The specimen stage can include a desorption region, wherein the desorption region is transparent to the laser beam, and wherein the laser source and the sampling probe are on opposite sides of a primary surface of the specimen stage.

A system for performing analysis of at least one analyte, the analyte being present in a solid specimen, can include a solvent dispensing and extraction system, the solvent dispensing and extraction system forming with a solvent a liquid microjunction between a portion of the solvent dispensing and extraction system and the solid specimen. A laser ablation system can be provided for administering ablating laser energy to the solid specimen, whereby ablated analyte will be accumulated in the solvent and can be extracted for analysis. The solvent dispensing and extraction system can further include a surface sampling probe for dispensing solvent to the specimen, the liquid microjunction being formed between the surface sampling probe and the specimen.

A system for performing analysis of at least one analyte present in a solid specimen, can include a laser source for emitting a laser beam toward a specimen to generate ablated analyte. A solvent dispensing and extraction system can be provided, the solvent dispensing and extract on system having an atomic force microscopy probe with a conduit for dispensing a solvent adjacent to a surface of the sample such that at least a portion of the ablated analyte can be accumulated in the solvent. The solvent dispensing and extraction system have structure for extracting the analyte-containing solvent for analysis.

A method of extracting an analyte from a specimen, can include the steps of providing a specimen supported by a specimen stage; providing a solvent dispensing and extraction system including a surface sampling probe for dispensing a solvent solution to the specimen; forming a liquid microjunction with the solvent between the surface sampling probe and the specimen; directing a laser beam at the specimen to ablate a portion of the analyte from the specimen; capturing the ablated analyte in the solvent liquid microjunction; and extracting the analyte-containing solvent for analysis. The method can further include the steps of analyzing a chemical composition of the extracted analyte, and repeating the ablating, extracting and analyzing steps for each of a plurality of target sites of the specimen.

A method of extracting an analyte from a specimen, can include the steps of providing a specimen supported by a specimen stage; providing a solvent dispensing and extraction system including a surface sampling probe for dispensing a solvent solution to the specimen; directing a laser beam through the surface sampling probe at the specimen to ablate a portion of the analyte from the specimen; capturing the ablated analyte after exposure to said laser beam in the solvent in the liquid microjunction; and, extracting the analyte-containing solvent. The method can include the steps of analyzing a chemical composition of the extracted analyte, repeating the ablating, extracting and analyzing steps for each of a plurality of target sites of the specimen.

A method of extracting an analyte from a specimen, can include the steps of providing a specimen supported by a specimen stage; providing a solvent dispensing and extraction system including a surface sampling, atomic force microscopy probe for dispensing a solvent solution to the specimen and for performing atomic force microscopy measurements; directing a laser beam at the specimen to ablate a portion of the analyte from the specimen; dispensing solvent through the probe; taking atomic force microscopy readings with the probe; capturing the ablated analyte in the dispensed solvent; and, extracting the analyte-containing solvent. The method can include the step of directing a laser beam at the specimen to ablate a portion of the analyte from the specimen. The method can include the steps of analyzing a chemical composition of the extracted analyte, and repeating the ablating, extracting and analyzing steps for each of a plurality of target sites of the specimen.

A method of extracting an analyte from a specimen can include the steps of providing a specimen; providing a solvent dispensing and extraction system including a surface sampling probe for dispensing a solvent solution to the specimen; dispensing a defined quantity of solvent through the probe onto the specimen, and then stopping the flow of solvent to the specimen; capturing the analyte in the solvent; and extracting the analyte-containing solvent. The method can further include the step of directing a laser beam at the specimen so as to ablate a portion of the analyte from the specimen, whereby the ablated analyte will be captured in the solvent. The method can include the steps of analyzing a chemical composition of the extracted analyte, and repeating the ablating, extracting and analyzing steps for each of a plurality of target sites of the specimen.

BRIEF DESCRIPTION OF THE DRAWINGS

A fuller understanding of the present invention and the features and benefits hereof will be obtained upon review of the following detailed description together with the accompanying drawings, in which:

FIG. 1 is

FIG. 17 is a schematic of an alternative embodiment.

FIG. 18 is a schematic of another alternative embodiment.

FIG. 19 is a schematic of another alternative embodiment.

FIGS. 27A-C are schematic diagrams of an embodiment and method of a surface sampling system using a droplet/suction technique with laser ablation.

DETAILED DESCRIPTION OF THE INVENTION

Figure 1:
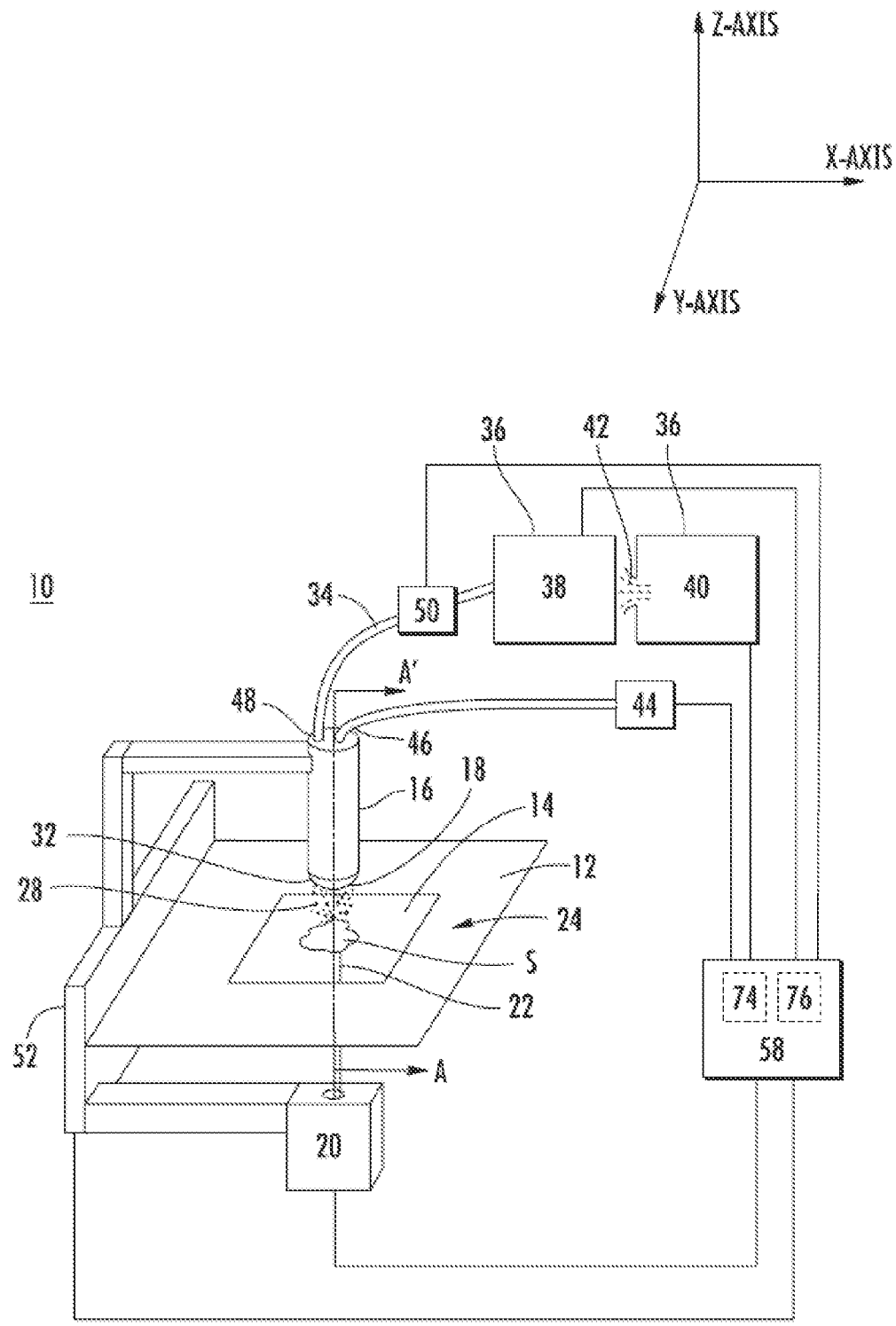
FIG. 1 is a schematic of a transmission geometry laser desorption system according to the invention.

The present invention is directed to systems and methods for desorption sampling and chemical analysis of a specimen. In particular, systems and methods for producing testing solutions of an analyte obtained through laser desorption of a specimen are described. The systems and methods described herein can also provide mapping the chemical composition of the specimen. It is noted that like and corresponding elements mentioned herein and illustrated in the figures are generally referred to by the same reference numeral. It is also noted that proportions of various elements in the accompanying figures are not drawn to scale to enable clear illustration of elements having smaller dimensions relative to other elements having larger dimensions.

As shown in the Figures, the system 10 for extracting an analyte from a specimen (S) can include a specimen stage 12 including a desorption region 14 that is transparent to a radiation wavelength (λ), a sampling probe 16 for suspending a solvent 18 above the specimen stage 12, and a laser source 20 for emitting a laser beam 22 centered at the radiation wavelength (λ) toward the specimen stage 12 or, more particularly, toward the desorption region 14 and a target site 26 of the specimen (S).

Figure 2:
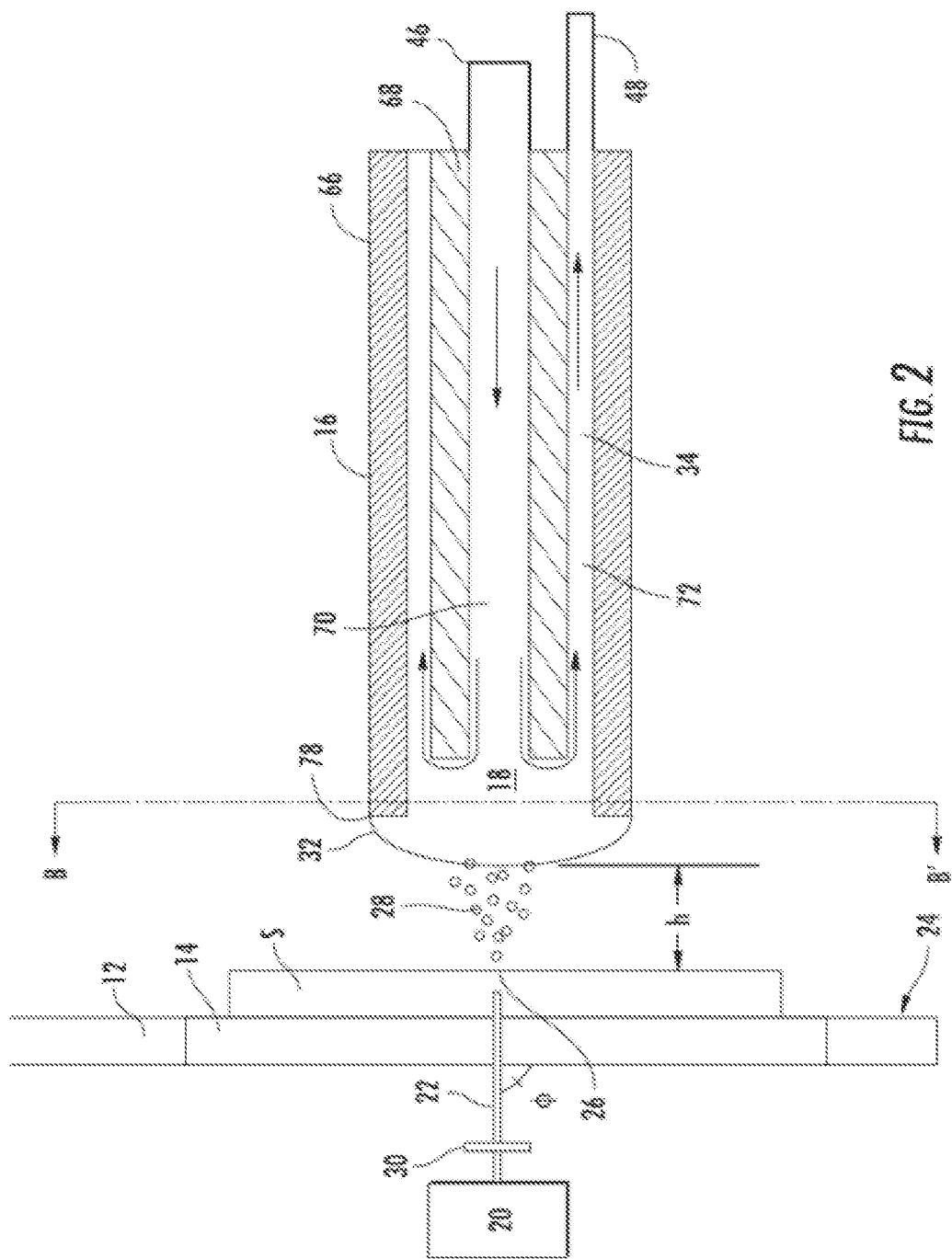
FIG. 2 is a cross-sectional view of the laser desorption system of FIG. 1 taken along cut line A-A', where the sampling probe has a dual capillary configuration.
Figure 3:
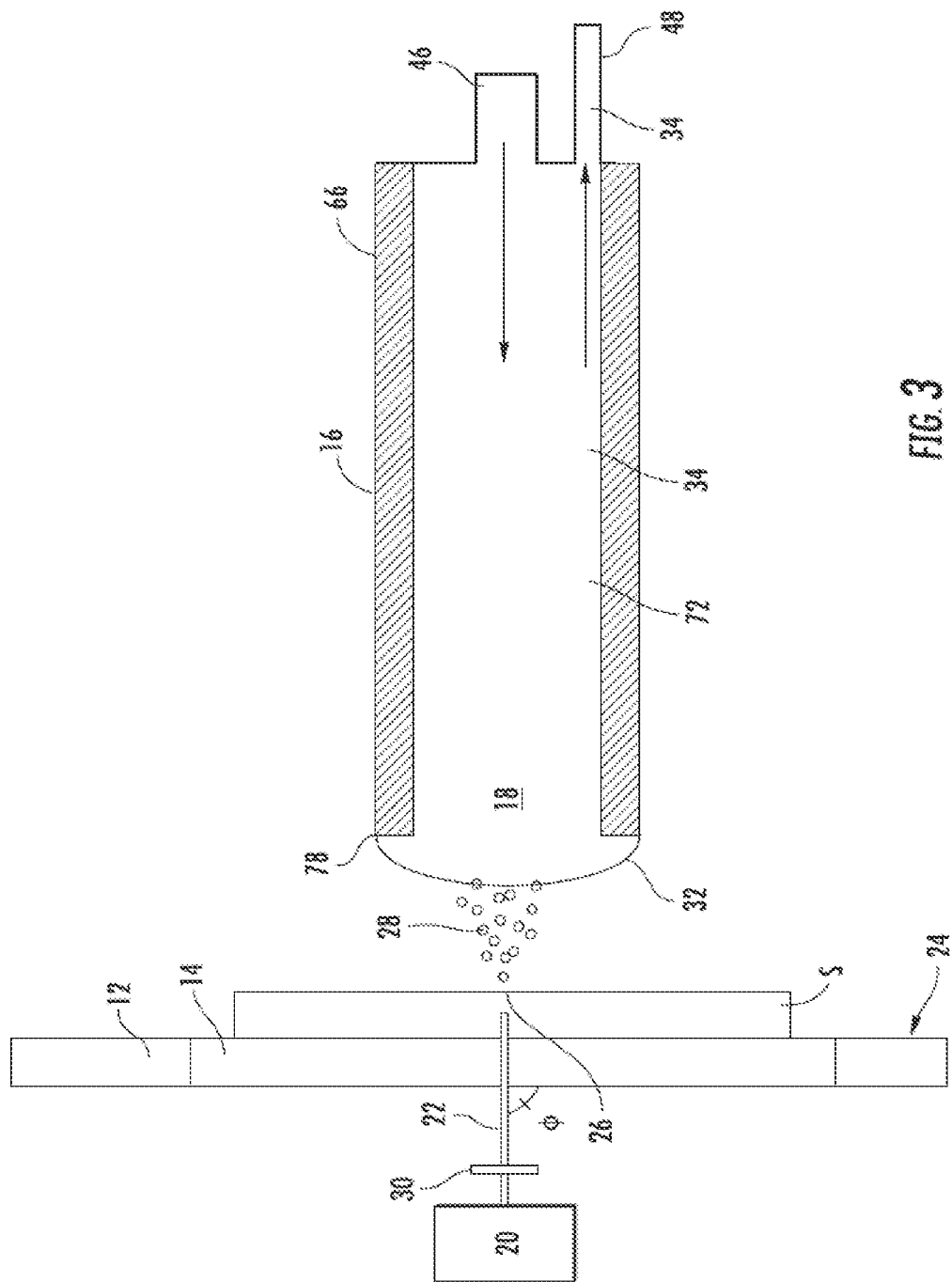
FIG. 3 is a cross-sectional view of the laser desorption system of FIG. 1 taken along cut line A-A', where the sampling probe has a single capillary configuration.

As shown in FIGS. 1-3, the laser source 20 and the sampling probe 16 can be on opposite sides of a primary surface 24 of the specimen stage 12. As shown in FIGS. 2 & 3, where the laser source 20 and the sampling probe 16 are on opposite sides of the primary surface 24, the incident angle (φ) of the laser beam 22 can be between 45 and 135°, or between 70 and 110°, or between 80 and 100°, or between 85 and 95°, or between 88 and 92°. As used herein, "primary surface" refers to the major surface of the specimen stage 12 that is proximate the sampling probe 16.

Figure 6:
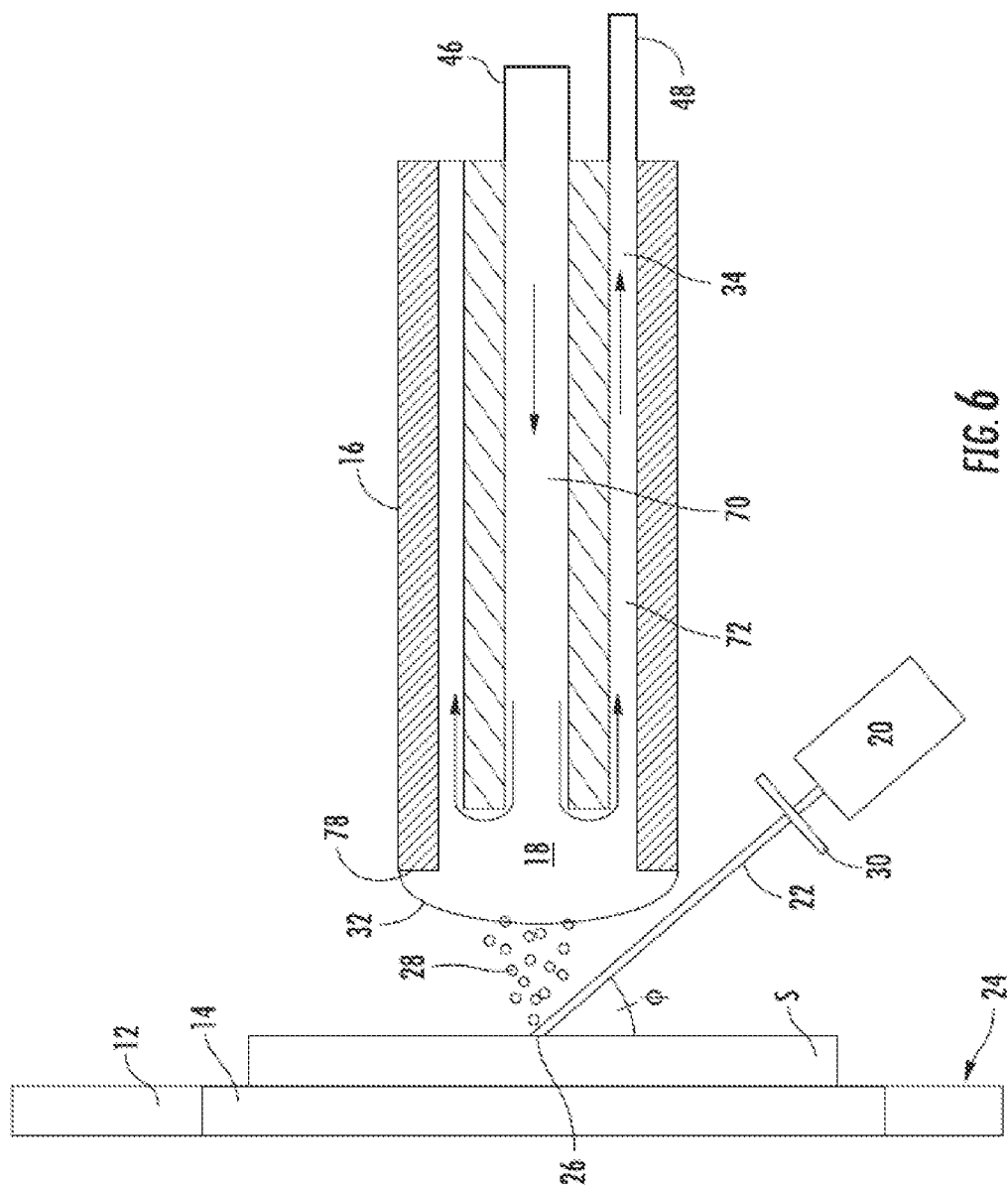
FIG. 6 is a cross-sectional view of the laser desorption system of FIG. 5 taken along cut line C-C', where the sampling probe has a dual capillary configuration.

As used herein, "desorption region" refers to that region of the specimen stage 12 where specimens to be sampled are positioned. In one exemplary specimen stage 12, the desorption region 14 can be an opening designed to receive a mounted specimen, e.g., a specimen mounted on a glass or quartz slide. In another exemplary specimen stage 12, which is shown in FIGS. 2 & 6, the desorption region 14 can be a glass or quartz insert that is coupled to the specimen stage 12. Alternately, the entire specimen stage 12 can be a desorption region.

As used herein, "transparent" refers to a material that transmits all or nearly all of a given wavelength of electromagnetic radiation, with little or no diffuse transmission, absorption or reflection. For example, the combined amount of diffuse transmission, absorption and reflection of a material that is transparent at a given wavelength can be 10% or less, 5% or less, 2.5% or less, 1% or less, or 0.1% or less for the given wavelength. It is also possible that the material transmits laser energy, such as in laser-induced acoustic desorption.

Regardless of where the laser source 20 is positioned with respect to the specimen stage 12, the laser beam 22 can be directed toward the desorption region 14 for a sufficient duration to evolve a desorbed analyte 28 from the target site 26. Where the desorbed analyte 28 is a gaseous analyte, the desorbed analyte 28 can be volatized molecules from the target site 26, pyrolytic decomposition products of molecules from the target site 26, or both. A unique feature this technique is the ability to use the laser desorption to desorb intact molecular species of both large molecules, e.g., >10,000 Da or 100,000 Da, or 1,000,000 Da, and small molecules, e.g., <10,000 Da, <1,000 Da, or even elemental ions.

As used herein, "desorbed analyte" refers to any gaseous, liquid or solid material that is evolved from the target site. For example, the desorbed analyte can be in a gaseous form, an aerosol form or even a particulate form.

The laser source 20 can be any appropriate gas or solid state laser emitting a laser beam of sufficient intensity and wavelength to evolve a desorbed analyte 28 from the target site 26. The laser beam 22 can propagate through the atmosphere or through an optical coupler 30, e.g., lenses or fiber optic wires. The optical coupler 30 can be positioned between the laser source 20 and the specimen stage 12. The wavelength of the laser source 20 can be selected in order to facilitate energy absorption by the target site 26.

As clearly seen in FIG. 6, a free surface 32 of the suspended solvent 18 can have the form of a meniscus. As the desorbed analyte 28 contacts the free surface 32, the analyte can mix with, e.g., dissolve in, the solvent 18 to form a testing solution 34. Although a liquid micro-junction can be formed during the desorption step, as shown in FIG. 2, the distance (h) between the free surface 32 and the specimen (S) can be a positive value, i.e., no liquid micro-junction. The distance (h) between the free surface 32 and the specimen can be between 1 μm and 3 mm, or between 50 μm and 2 mm or between 100 μm and 1 mm. The distance can be 1 mm or less, or 750 μm or less, or 500 μm or less, or 250 μm or less, or 150 μm or less.

As shown in FIGS. 2 & 6, the sampling probe 16 can include an outer capillary tube 66 and an inner capillary tube 68 disposed co-axially within the outer capillary tube 66. The inner and outer capillary tubes 68, 66 can define a solvent capillary 70 and a sampling capillary 72 in fluid communication with one another at a distal end of the probe 16. As shown in FIGS. 2 & 6, the tip of the inner capillary tube 68 can be recessed within the outer capillary tube 66. Although FIGS. 2 & 6 show the solvent capillary 70 defined by the inner capillary tube and the sampling capillary 72 defined by the annular space between the inner and outer capillary tubes 68, 66, it should be understood that this flow arrangement can be reversed.

Figure 7:
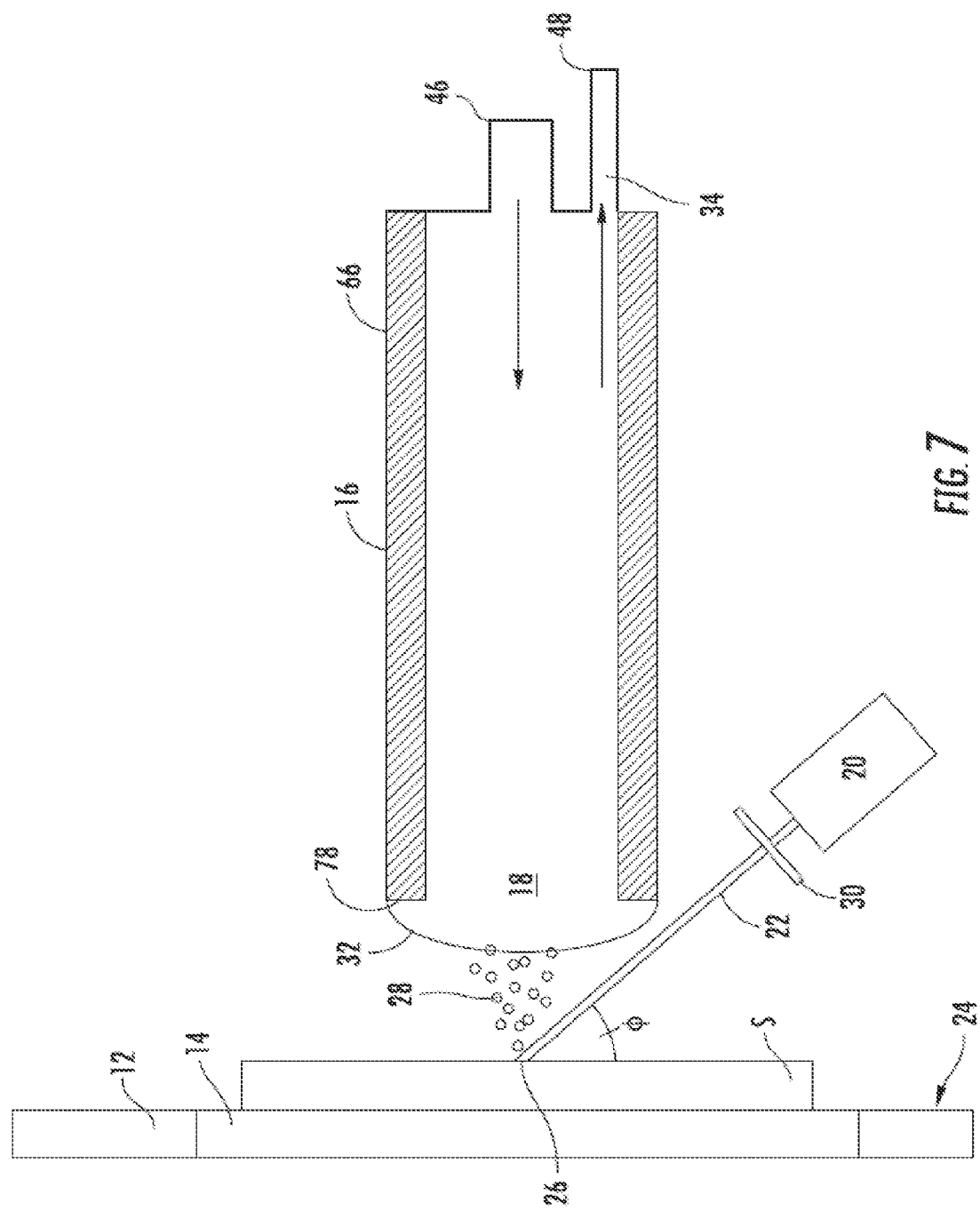
FIG. 7 is a cross-sectional view of the laser desorption system of FIG. 5 taken along cut line C-C', where the sampling probe has a single capillary configuration.

As shown in FIGS. 3 & 7, the sampling probe 16 can include a single capillary 66 with a solvent inlet 46 and a sampling outlet 48. In the single capillary embodiment, the sampling probe 16 does not include an inner capillary tube in fluid communication with the single outer capillary 66. In an alternate example, the solvent inlet 46 and sampling outlet 48 are essentially combined and both functionalities are provided through a single coupling 46, 48. For example, the example shown in FIGS. 8A-F would only require one coupling that could be used to draw in a solvent 18 through the tip 78 of the probe 16 and then dispense the testing solution 34 through the same tip 78.

The system 10 can also include an analytical instrument 36 for determining a chemical composition of an analyte at a target site 26 on a specimen (S) being analyzed via the testing solution 34. The solvent 18 can be in fluidic communication with a solvent pump 44 via a solvent inlet 46. The solvent 18 can be in fluid communication with the analytical instrument 36 via a sampling outlet 48. The solvent 18 and/or testing solution 34 can be in fluid communication with the analytical instrument 36.

A sampling pump 50 can be provided in order to control the output rate from the sampling outlet 48. This enables the user to control the flow rates at the sampling outlet 48 and the solvent inlet 46, which can be the same or different flow rates. Although shown separately, the sampling pump 50 can be incorporated into the probe 16 or any downstream device, such as an analytical instrument 36. The pumps 44, 50 can be any form of pump including, but not limited to velocity pumps, buoyancy pumps, syringe pumps, positive displacement pumps, venturi pumps, and gravity pumps. Of particular interest, the pumps 44, 50 can be syringe pumps, positive displacement pumps, nebulization or electrospraying devices, or chambers with sufficient pressure differentials to induce fluid flow.

Figure 5:
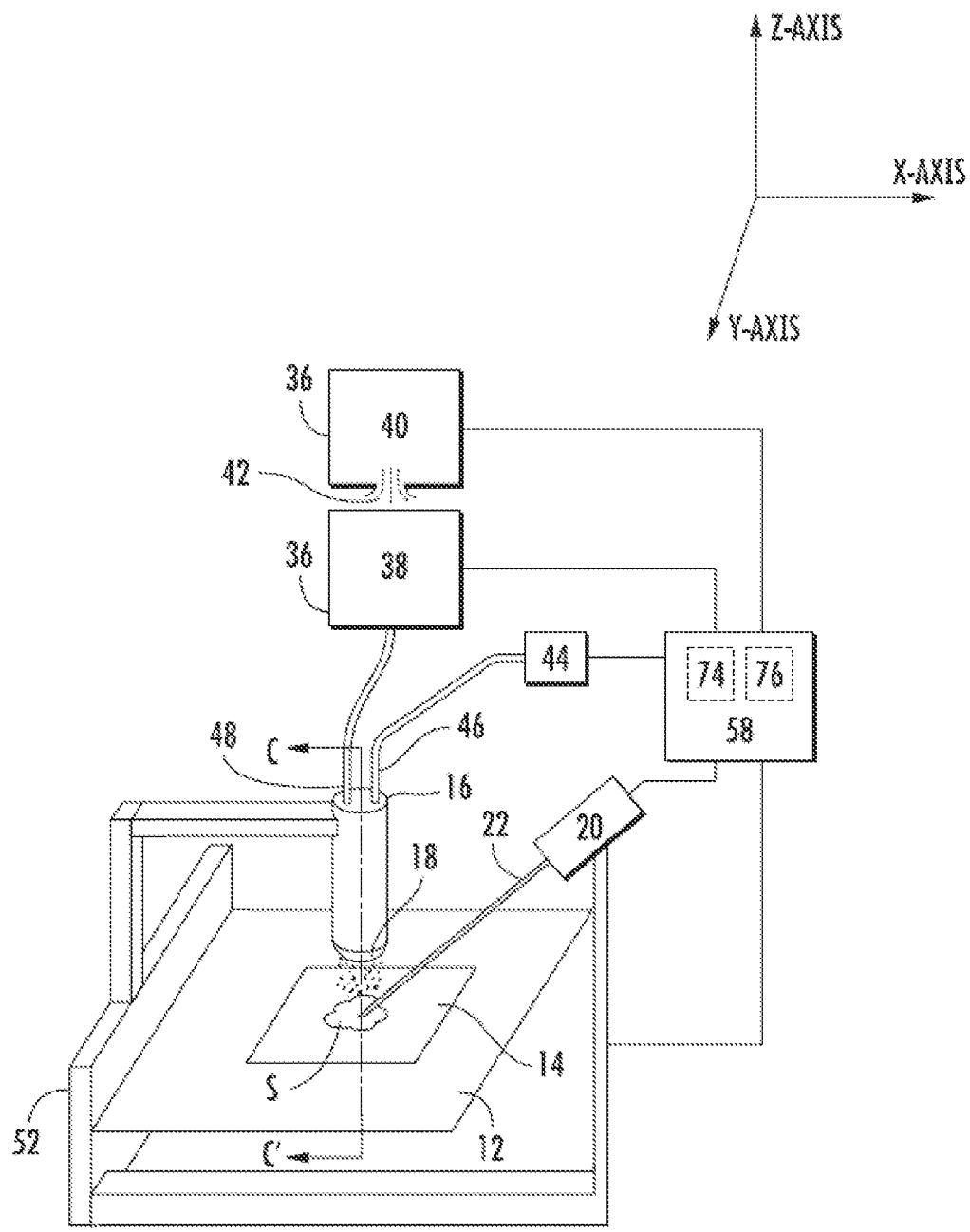
FIG. 5 is a schematic of a reflective geometry laser desorption system according to the invention.

The analytical instrument 36 can be a mass spectrometer, an ionization source, a separation method, or a combination thereof. As shown in FIGS. 1 & 5, the analytical instrument 36 can be an ionization source 38 and a mass spectrometer 40. The mass spectrometer 40 can be arranged to receive an ionized analyte 42 from the ionization source 38.

The analytical instrument 36 can be any instrument utilized for analyzing analyte solutions. Exemplary analytical instruments include, but are not limited to, mass spectrometers, ionization sources, spectroscopy devices, separation methods, and combinations thereof. Exemplary ionization sources include, but are not limited to electrospray ionization, atmospheric pressure chemical ionization, electrospray chemical ionization (ESCi), atmospheric pressure photo-ionization or inductively coupled plasma. Exemplary separation methods include, but are not limited to liquid chromatography, solid phase extraction, HPLC, capillary electrophoresis, or any other liquid phase sample cleanup or separation process. Exemplary mass spectrometers ("MS") include, but are not limited to, sector MS, time-of-flight MS, quadrupole mass filter MS, three-dimensional quadrupole ion trap MS, linear quadrupole ion trap MS, Fourier transform ion cyclotron resonance MS, orbitrap MS and toroidal ion trap MS.

The system can include a stepper mechanism 52 configured to sequentially direct the laser beam 22 at a plurality of target sites 26 of a specimen (S) supported by the specimen stage 12. The stepper mechanism 52 can also be configured to provide relative motion between the specimen stage 12 and the sampling probe 16.

As used herein, a stepper mechanism has its standard meaning in the art and should be understood to include any device or combination of devices for changing the relative position between the sampling probe 16, the specimen stage 12 or the specimen (S) supported thereon, and/or the laser source 20. For example, the specimen stage 12 can be coupled to the stepper mechanism 52 and move the sample stage 12 laterally (X-axis), transversely (Y-axis), and vertically (Z-axis) along a sampling path 54. Alternately, the probe 16 can be coupled to the stepper 52, which can move the probe 16 laterally, transversely and vertically along the sampling path 54. Finally, the laser source 20 can be coupled to the stepper 52, which can direct the laser beam 22 along the sampling path 54 by rotating the laser source 20 and moving the laser source 20 laterally, transversely and vertically.

Figure 4:
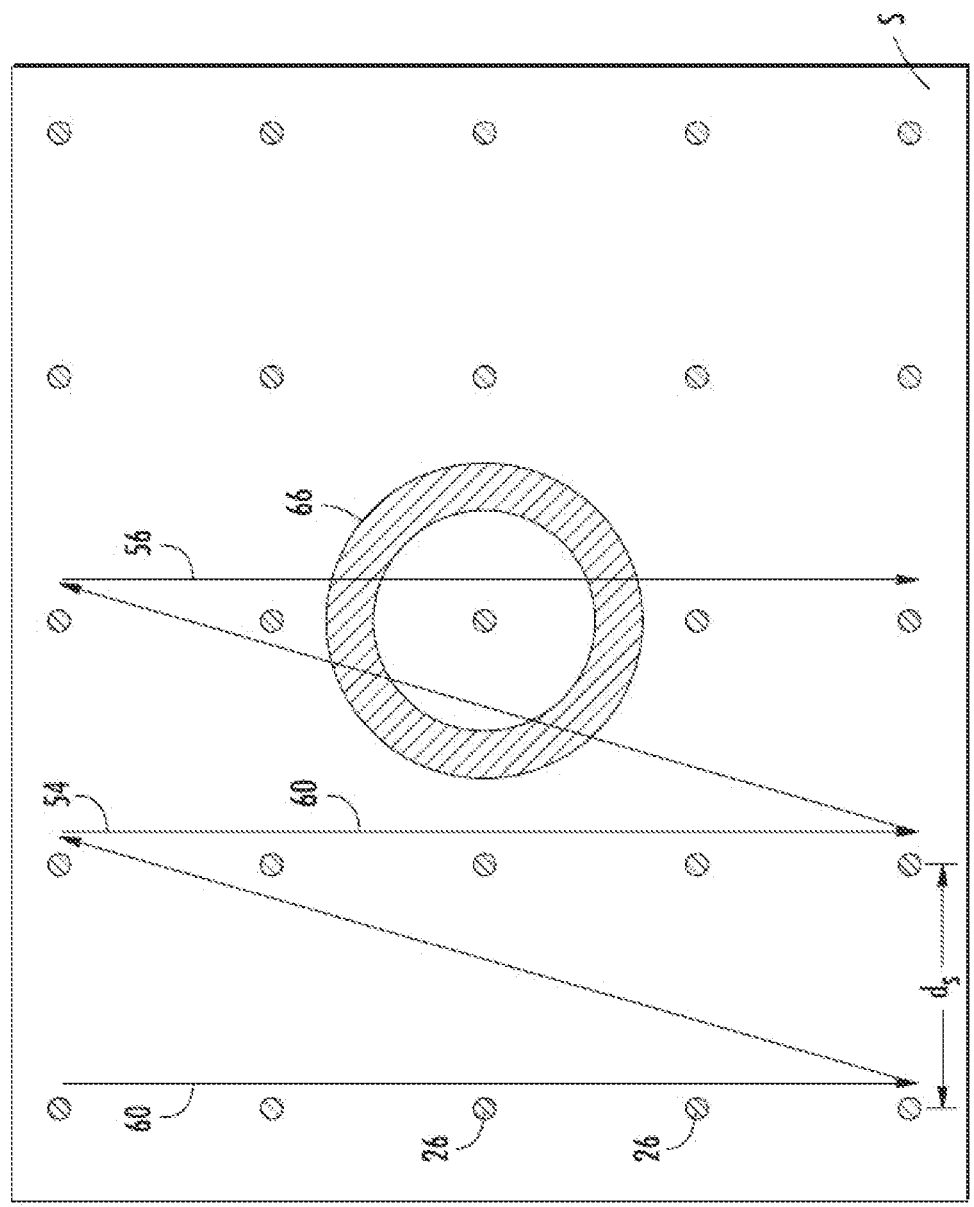
FIG. 4 is a cross-sectional view of the laser desorption system of FIG. 2 taken along cut line B-B', including a depiction of the sampling path.

As shown in FIG. 4, a sampling path 54 can be a sampling regime that includes a plurality of target sites 26. FIG. 4 only shows the lateral and transverse components of the sequence for sampling the target sites 26 along the sampling path 54; however, the sampling path 54 can also include a vertical component. For example, as shown in FIGS. 8A-F, the probe 16 can be positioned proximate a first target site 26 in order to capture the desorbed analyte 28 and can then be repositioned proximate an electrospray ionization (ESI) chip 56 so that the testing solution 34 can be dispensed through the ESI chip 56.

The articulation by the stepper 52 between sequential target sites 26 can occur with the laser beam 22 on or with the laser beam 22 off. Thus, turning the laser beam 22 off during articulation between target sites 26 allows sampling along a sampling path 54 that includes discrete target sites 26 as shown in FIG. 4. Whereas, maintaining the laser beam 22 during articulation between target sites 26 allows sampling of linear target sites 60, i.e., target lines, as also shown in FIG. 4. The controller 58 can be configured for causing the stepper mechanism 42 to perform each of the sampling sequences described anywhere herein.

In some examples, the target sites 26 can be sampling lines 60. In general, the plurality of sampling lines 60 will be parallel and spaced apart by a distance ($d_s$). In such an embodiment, the specimen (S) can be laser desorbed, i.e., sampled, along an entire sampling line 60. The laser beam 22 can be turned off and repositioned to travel along the next sampling line 60.

The sampling path 54 can be an array of regularly spaced target sites 26. As used herein, "regular spacing" and "regularly spaced" are used interchangeably and refer to spacing where the distance between adjacent target sites 26 in a line is equal or approximately equal along the length of the line, as shown in FIG. 4. Regular spacing also refers to instances where the same target site is part of two or more lines with regular spacing, which is also shown in FIG. 4. Of interest, the distance between adjacent target sites 26 or adjacent sampling lines 60 can be 100 µm or less, or 50 µm or less, or 25 µm or less, or 10 µm or less, or 5 µm or less.

As shown in FIGS. 8A-F, the stepper mechanism 52 can also be configured (i) to sequentially position the sampling probe 16 to capture a desorbed analyte 28 that is laser desorbed from each of a plurality of target sites 26 with a suspended solvent 18 to form a testing solution 34 and (ii) to discharge the testing solution 34 to a testing device 62. As used herein, the phrase "testing device" includes not only analytical instruments 36, but also devices useful for intermediate processing steps. For example, the testing device 62 could be a plate with a plurality of wells that allows the analyte in the testing solution 34 to react or culture. Exemplary testing devices, other than analytical instruments, include UV visible spectrometer, fluorometer, pH measuring devices, conductivity measuring devices, etc. It is to be understood that all analytical instruments 36 are testing devices 62.

Figure 8A:
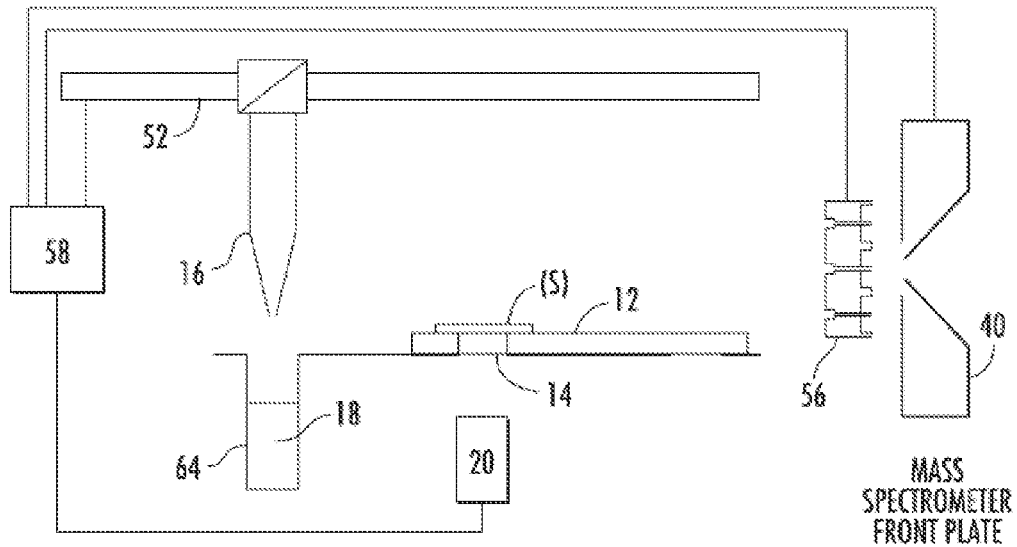
FIGS. 8A-F show a sampling sequence of a laser desorption system according to the invention where the testing solution is dispensed from the tip of the sampling probe.
Figure 8B:
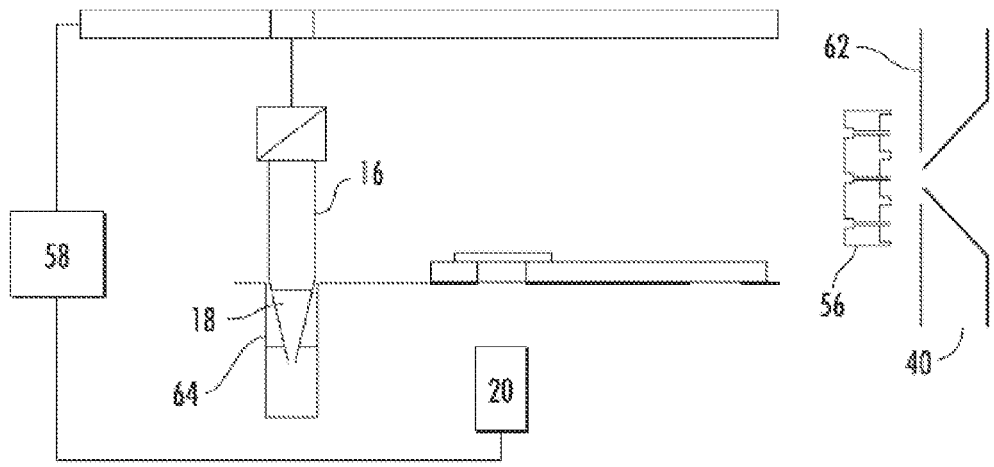
Figure 8C:
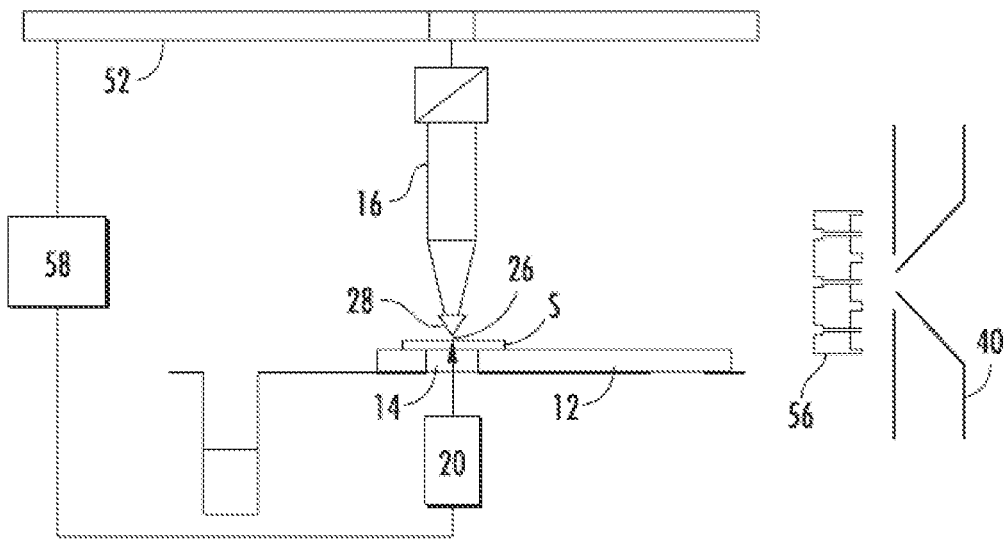
Figure 8D:
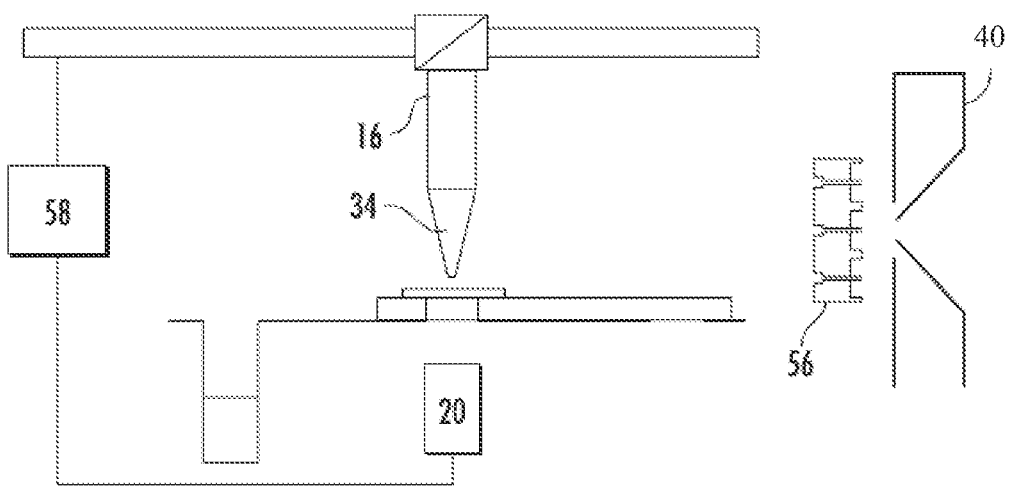
Figure 8E:
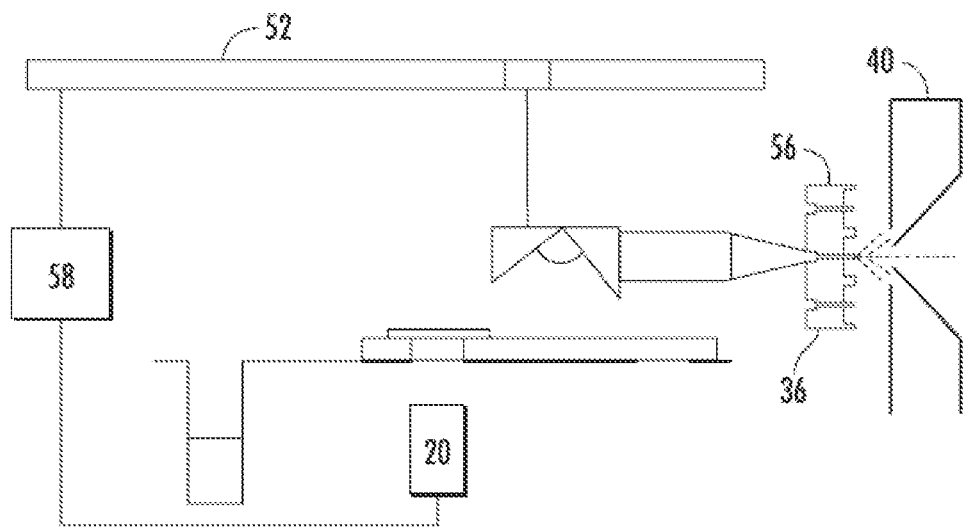
Figure 8F:
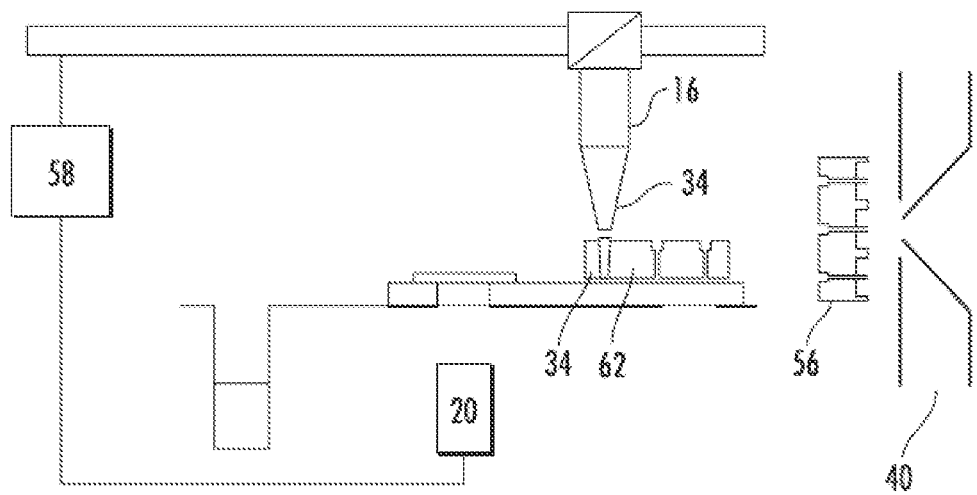

As shown in FIGS. 8A-F, the testing solution 34 can be discharged from a distal end of the sampling probe 16. As shown in FIG. 8A, an empty sampling probe 16 can be suspended over a solvent reservoir 64 by the stepper mechanism 52. The stepper mechanism 52 can then lower the sampling probe 16 into the solvent reservoir 64 and solvent 18 can be drawn into the sampling probe 16, as shown in FIG. 8B. The sampling probe 16 can then be positioned above the target site 26 and the laser source 20 actuated to direct a laser beam 22 at the target site 26, as shown in FIG. 8C. The laser beam 22 can cause the formation of a desorbed analyte 28. As shown in FIG. 8D, the desorbed analyte 28 can contact and mix with the solvent 18 to form a testing solution 34. The testing solution 34 can then be dispensed into a testing device 62 such as an ESI ionization chip 56 and mass spectrometer 40 or into a testing device 62, such as a well plate, as shown in FIGS. 8E and 8F, respectively.

As shown in FIG. 8E, the sampling probe 16 can be repositioned proximate to an analytical instrument 36 and the testing solution 34 can be dispensed into the analytical instrument 36. Alternately, the sampling probe 16 can be repositioned proximate to a well plate 62 and some or all of the testing solution 34 can be dispensed into one or more wells of the well plate 62, as shown in FIG. 8F. In the embodiment of FIG. 8F, the testing solution 34 can undergo further processing, incubating and analyzing steps after being dispensed into the well plate 62. The process can be repeated for each of a plurality of target sites 26. The tip of the probe 16, e.g., a pipette tip, can be replaced for each target site 26.

The data from each of the target sites 26 can be stored on a computer readable storage, such as are known in the art. The data can be compiled to form a two-dimensional map, or surface, of the composition of the specimen by plotting the data according to the position of the array of target sites from which the data was obtained. The data can be displayed on an output device, such as a monitor, print r, smartphone or the like.

The system 10 can include a controller 58 communicatively coupled to one or more of the laser source 20, the stepper mechanism 52, the solvent pump 44, the sampling pump 50 and any analytical instruments 36. The controller 58 can also be configured for causing the system 10 components described herein to carry out any of the method steps or processes described herein. For example, the controller 58 can be configured to cause the stepper mechanism 42 to produce any relative motion between the laser source 20, the specimen stage 12, including the desorption region 14, and the sampling probe 16, described herein.

The controller 58 can include a computer readable storage 74 in communication with a processor 76. The computer readable storage 74 can include computer executable instructions for carrying out the methods described herein. The processor 76 can be configured to execute the computer executable instructions stored on the computer readable storage 74. In addition, although shown as a single box that includes a single computer readable storage 74 and a single processor 76, it should be understood that the controller 58 can be spread across multiple devices and can include multiple computer readable storages and processors.

As used herein, sequentially articulate refers to automatically moving the probe 12, the sample stage 40, or both along the sampling path 52 to a plurality of target sites 44. In some instances this articulation can be continuous while in others there will be intermittent pauses. For example, the articulation may be paused while the desorbed analyte 28 contacts the free surface 32 of the solvent 18 in order to ensure an adequate amount of analyte is present in the testing solution 34 or to provide adequate separation between ionized analyte 42 samples being fed to an analytical instrument 36, such as a mass spectrometer 40.

The system 10 can also include a specimen stage 12, a sampling probe 16 configured to suspend a solvent 18 in the form of an uninterrupted meniscus 32 above the specimen stage 12, a laser source 20, and a stepper mechanism 58 configured to provide relative motion between the laser source 20 and the specimen stage 12. As shown in FIGS. 5-7, the laser source 22 and the sampling probe 16 can both be on a primary surface-side 24 of the specimen stage 12.

In instances where the laser source 20 and the sampling probe 16 are on the primary surface-side 24 of the specimen stage 12, the incident angle (θ) of the laser beam 22 can be between 0 and 90°, or between 30 and 80°, or between 35 and 70°. The sampling probe 16 can have a dual capillary arrangement or single capillary arrangement, as shown in FIGS. 6 & 7, respectively.

As used herein, the phrase "uninterrupted meniscus" refers to a continuous meniscus that is not interrupted by a part of the probe 16. For example, as shown in FIGS. 6 & 7, the meniscus 32 extends from the tip 78 of the outer capillary tube 66 and is not interrupted by the interior capillary tube 68. In addition, the flow regime and flow rates shown in FIGS. 6 & 7 are such that the flow of the testing solution 34 exiting the probe 16 does not disrupt the shape of the meniscus 32.

The invention is also drawn to a method of extracting an analyte from a specimen (S). The method can include providing a specimen (S) supported by a desorption region 14 of a specimen stage 12; desorbing an analyte from a target site 26 of the sample (S) with a laser beam 22 centered at a radiation wavelength ($\lambda$); and capturing the desorbed analyte 28 with a suspended solvent 18 to form a testing solution 34. The desorption region 14 can be transparent to the radiation wavelength ($\lambda$). The specimen (S) and the laser source 20 emitting the laser beam 22 can be on opposite sides of a primary surface 24 of the specimen stage 12. The method can also include analyzing a chemical composition of the desorbed analyte 28.

The desorbing, capturing and analyzing steps can be repeated for each of a plurality of target sites 26 of the specimen (S), e.g., each target site 26 along the sampling path 54. A chemical property of the analyte collected from each target site 26 can be plotted. The relevant chemical property can be any exogenous or endogenous property related to the specimen (S) being evaluated, including a property of a molecule or chemical component for each of the target sites 26. Properties of interest include, but are not limited to, concentration of a molecule or decomposition product, the relative ratio of two molecules (such as compound and reaction product of the compound), and the relative ratio of decomposition products.

For example, the property of interest can be the concentration of a chemical component, such as a pharmaceutical and its metabolites, at each target site 26. By arranging the data for each target site spatially within the specimen (S) a two-dimensional surface can be plotted.

In another example, the method can include desorbing an analyte from a target site 26 of a specimen (S) with a laser beam 22 centered at a radiation wavelength ($\lambda$); capturing the desorbed analyte 28 with a solvent 18 suspended in the form of an uninterrupted meniscus 32 above the specimen (S) to form a testing solution 34; and dispensing the testing solution 34 to a testing device 62. The sample (S), the laser beam 22 or both can be automatically, sequentially articulating to sample a second target site 26 and the desorbing, capturing and dispensing steps can be repeated for the second target site 26 of the specimen (S).

The laser source 20 and the sampling probe 16 can both be on the primary surface-side 24 of the specimen stage 12. Alternately, the laser source 20 and the sampling probe 16 can be on opposite sides of the specimen stage 12.

EXAMPLES

Example 1

Reflective Geometry, Dual Capillary Sampling Probe

The reflective geometry data was gathered using an arrangement similar to that shown in FIG. 6. In the probe used in the examples, the outer diameter and inner diameter of the outer capillary were ~635 µm and ~330 µm, respectively, while the outer diameter and inner diameter of the inner capillary were ~254 µm and ~127 µm, respectively.

The laser beam was propagated through a 400 μm fiber optic cable and then passed through a 35 mm focusing lens onto the target site. The impingement angle (θ) was 45°, the laser beam wavelength was 337 nm and the fluence of the beam was 80 mJ/cm$^2$. The solvent utilized was a 50:50 mixture of acetonitrile and water and the solvent flow rate was 13 μL/min.

Figure 9:
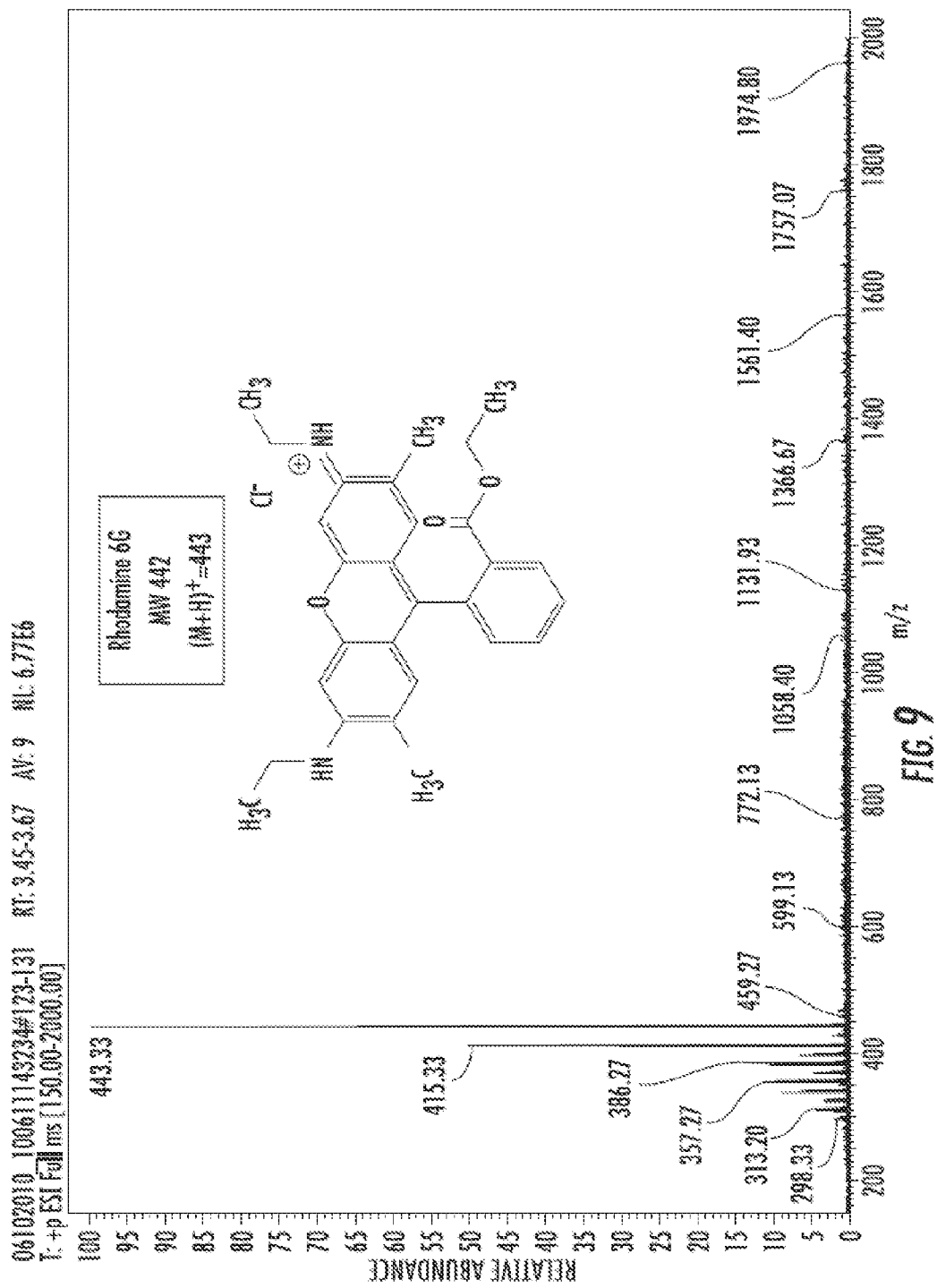
FIG. 9 shows relative abundance versus m/z for a rhodamine 6G ($M_w$=442) sampling analyzed using a reflective geometry laser desorption system according to the invention.

FIG. 9 shows the mass spectrometer abundance versus m/z data where the specimen was rhodamine 6G, which has a molecular weight of 442 g/mol, on a glass slide. The data clearly shows the protonated form of rhodamine 6G at m/z=443 as the base peak in the mass spectrum. These results correspond well with known data for rhodamine 6G.

Figure 10:
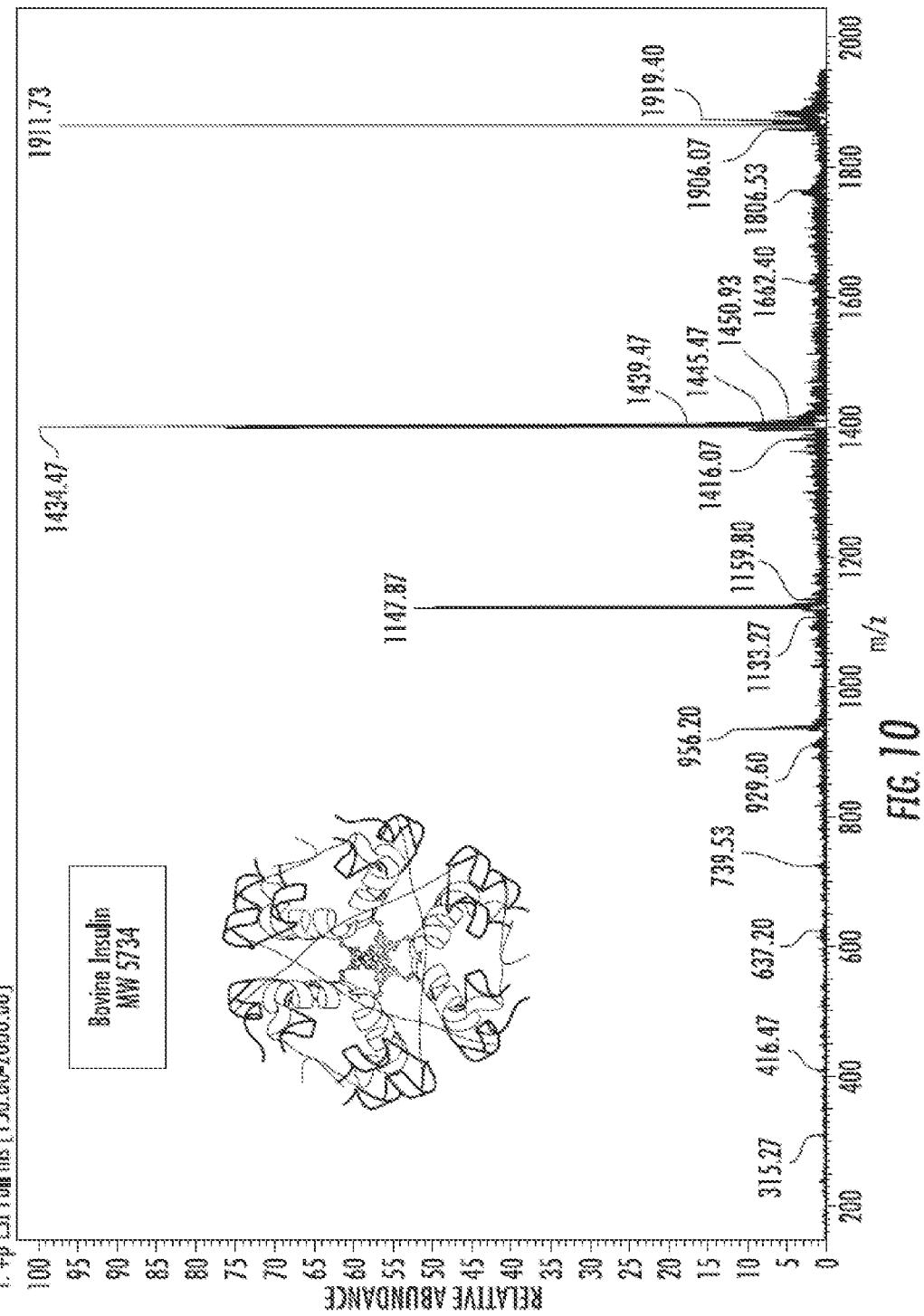
FIG. 10 shows relative abundance versus m/z for a bovine insulin ($M_w$=5734) sampling analyzed using a reflective geometry laser desorption system according to the invention.

FIG. 10 shows the mass spectrometer relative abundance versus m/z data where the specimen was 340 pmol of bovine insulin with a molecular weight of 5734 g/mol on a glass slide. The relevant peaks include m/z=956, m/z=1147, m/z=1434, and m/z=1911, which correspond to the +6, +5, +4 and +3 charge states of bovine insulin, respectively. This result is consistent with known charge states for the electrospray spectrum of bovine insulin. This is of particular interest because conventional laser desorption techniques, such as MALDI, typically exhibit only the +1 charge state. The data shows that the disclosed method and system are capable of desorbing and capturing analytes with a wide range of molecular weights and multiple charging of molecules, such as proteins.

Example 2

Transmission Geometry, Dual Capillary Sampling Probe

The transmission geometry data was gathered using an arrangement similar to that shown in FIG. 2. The laser beam was propagated through a 400 μm fiber optic cable and then passed through a 35 mm focusing lens toward the target site. The impingement angle (φ) was 90°, the laser beam wavelength was 337 nm and the fluence of the beam was 80 mJ/cm$^2$. The probe tip was positioned 0.5 mm from the sample and the solvent utilized was a 50:50 mixture of acetonitrile and water. The specimen stage included a desorption region made of quartz and the energy transmitted through the quartz was 100 μJ.

Figure 11:
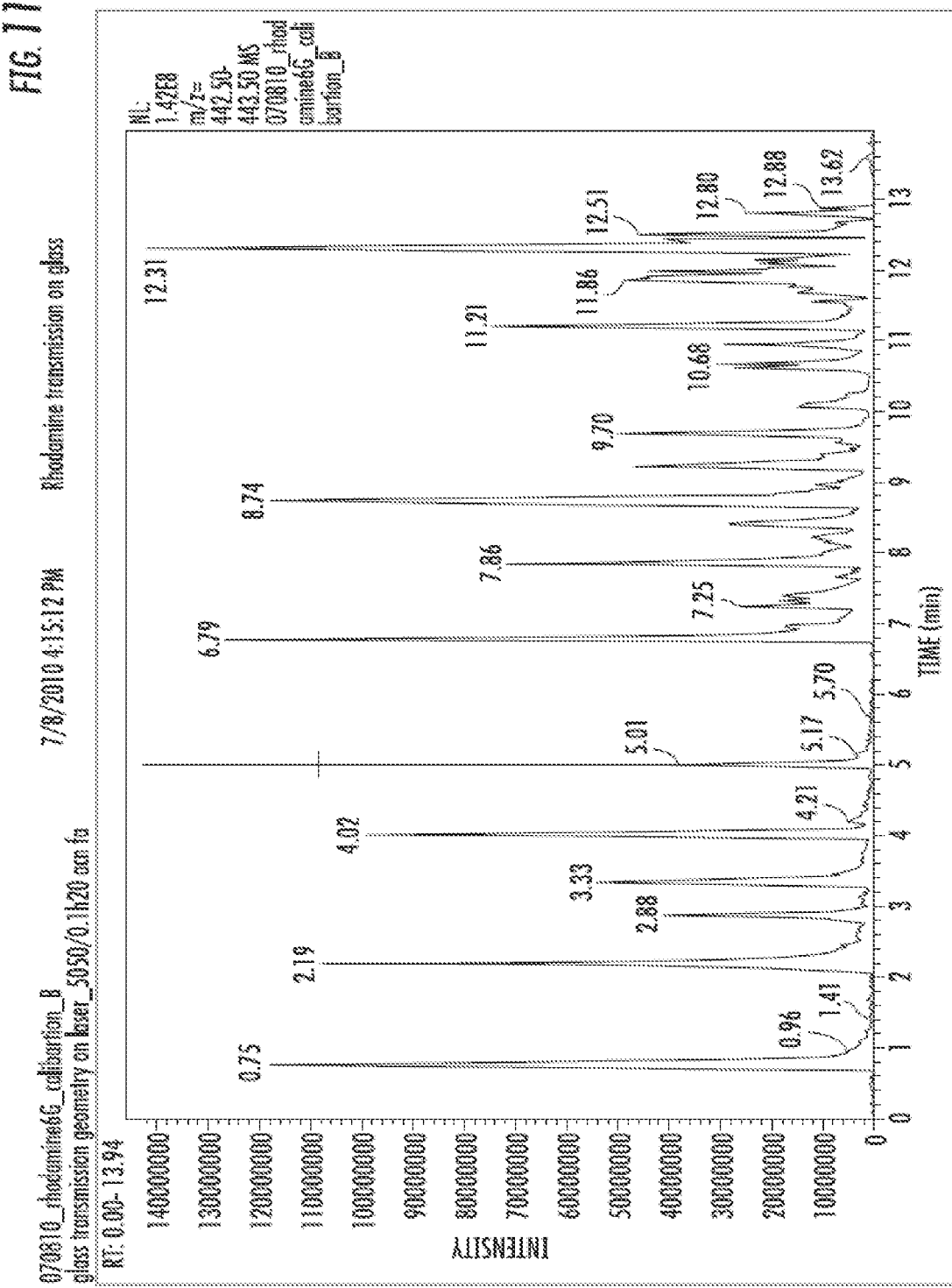
FIG. 11 shows intensity versus time data for a rhodamine 6G sample on glass obtained using a transmission geometry laser desorption system according to the invention.
Figure 12:
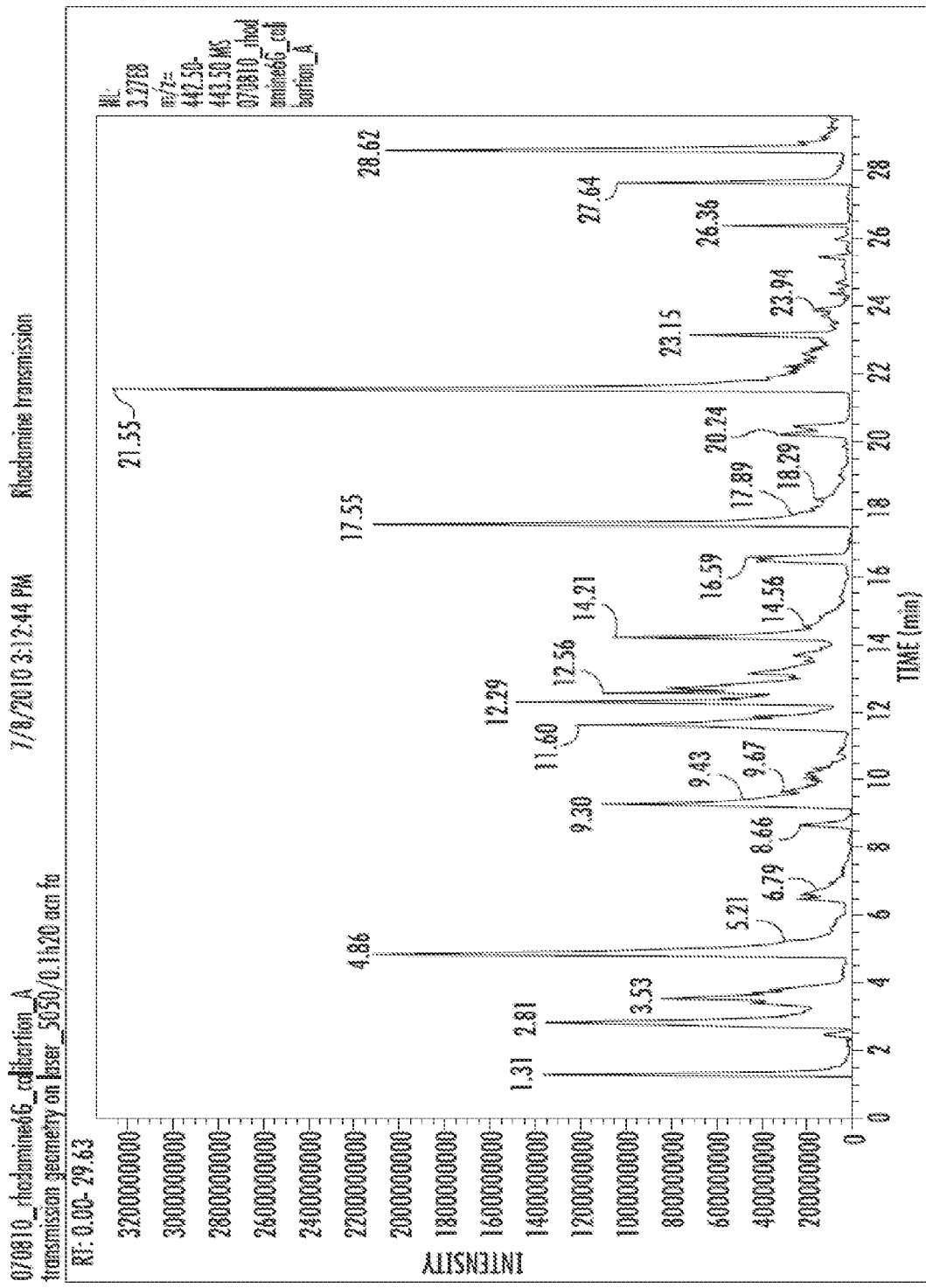
FIG. 12 shows intensity versus time data for a rhodamine 6G sample on quartz obtained using a transmission geometry laser desorption system according to the invention.

FIGS. 11 & 12 shows the mass spectrometer intensity versus time data for a rhodamine 6G sample on a glass slide and a quartz slide, respectively. The rhodamine 6G signal level on glass was approximately $1.4 \times 10^8$, while the signal level on quartz was approximately $3.2 \times 10^8$. In contrast, the signal intensity for rhodamine 6G on a glass slide using the reflective geometry was $1 \times 10^7$, or an order of magnitude less than using the transmission geometry. Thus, the transmission geometry is superior to the reflective geometry. This is particularly true where the desorption region and specimen slide are formed from quartz.

Example 3

Transmission Geometry, Single Capillary Sampling Probe

Sampling

This transmission geometry data was gathered using an arrangement similar to that shown in FIG. 3. The laser beam and focusing lens system was the same as that used in Example 2. The sampling probe was a 10 μL syringe loaded with 3 μL of solvent. The solvent composition was 49.95/49.95/0.1 water/acetonitrile/formic acid. The tip of the syringe was positioned 0.5 mm above the sample surface.

The laser was fired and 1 μL of solvent was dispensed from the syringe at a rate of 16 nL/sec, i.e., desorption step of approximately 1 minute. After the desorption step, the droplet hanging from the syringe tip was drawn into the syringe at a rate of 0.1 μL/sec for two (2) seconds. The testing solution in the syringe was then dispensed into an analytical instrument at a rate of 1 μL/s.

Mass Spectrometer Results

Figure 13A:
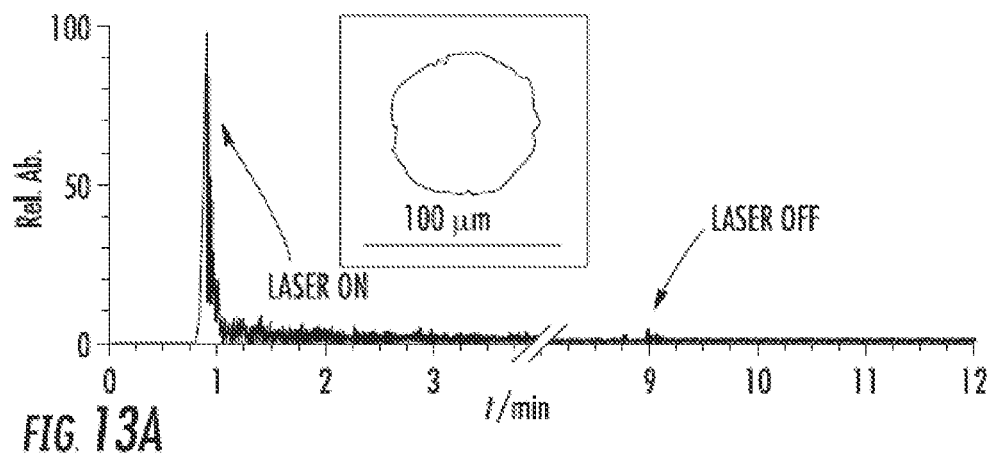
FIGS. 13A-C show (a) relative abundance versus time data for a rhodamine 6G sample on glass using a transmission geometry with a single capillary sampling device, (b) relative abundance versus m/z data for a testing solution collected using the laser desorption described herein, and (c) relative abundance versus m/z data for a control testing solution where a laser beam was not applied to the specimen.
Figure 13B:
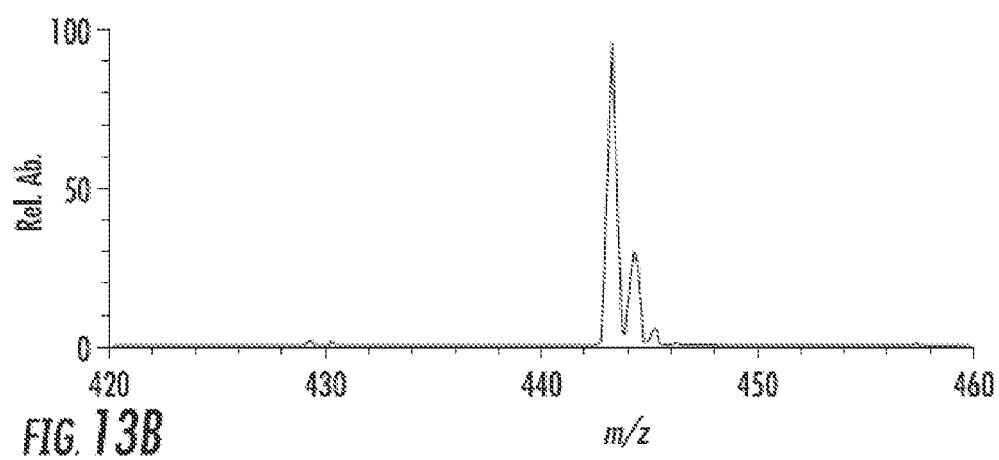
Figure 13C:
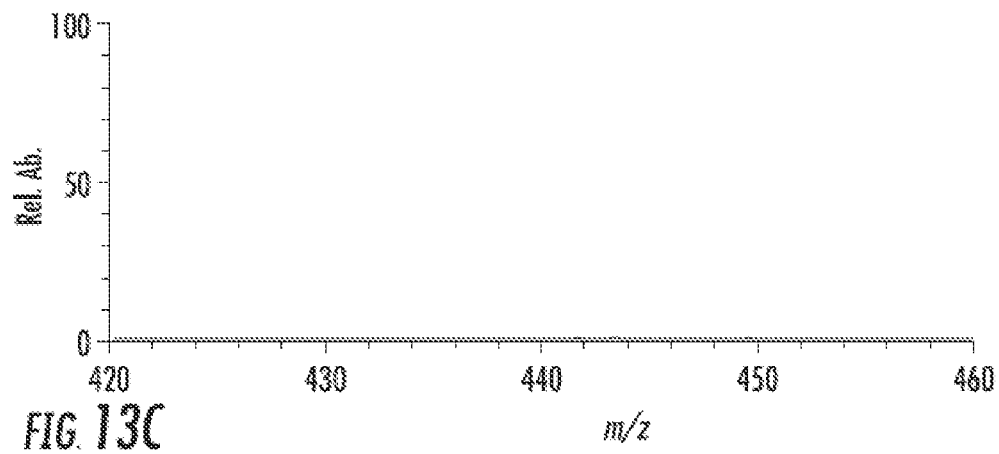

In the first part of this Example, testing solutions were collected both with and without the laser beam. The target analyte in both cases was rhodamine 6G and the testing solutions were injected into an electrospray ionization source that was operatively coupled to a mass spectrometer. FIG. 13(a) shows the extracted ion chromatogram generated using the ion intensity for m/z=443. At the far left is the peak resulting when a testing solution collected with the laser beam on (Sample A) was injected into the ESI source, while the point at 9 minutes shows there was no peak when a testing solution collected without the laser beam (Sample B) was injected into the ESI source. The inset of FIG. 13(a) shows an approximately 70 μm-diameter ablated area resulting from the laser desorption. FIGS. 13(b) and (c) show the relative abundance versus m/z data for Sample A and Sample B, respectively.

HPLC+Mass Spectrometer Data

Figure 14:
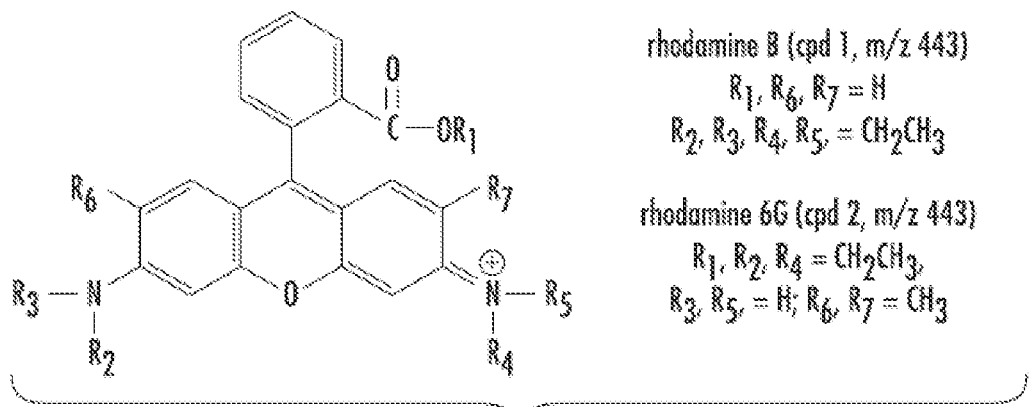
FIG. 14 shows the chemical structures of rhodamine B and rhodamine 6G.

In the second part of this Example, the target analyte included a 50:50 mass ratio of rhodamine B and rhodamine 6G, the chemical structures of which are shown in FIG. 14. The testing solution was collected as described in this Example and then injected into an HPLC device that was directly linked to an electrospray ionization source that was directly linked to a mass spectrometer. The HPLC was a Waters PAH C18 5 μm with a 2×150 mm column. The HPLC program was isocratic and the flow rate of the carrier gas was set to 200 μL/min.

Following desorption, a 70 μm diameter ablated area was observed. Based on a 1 mm diameter circular target site formed using a 10 μL rhodamine B/6G sample, this means that the amount of desorbed analyte was approximately 10.88 ng or 24.6 pmol.

Figure 15A:
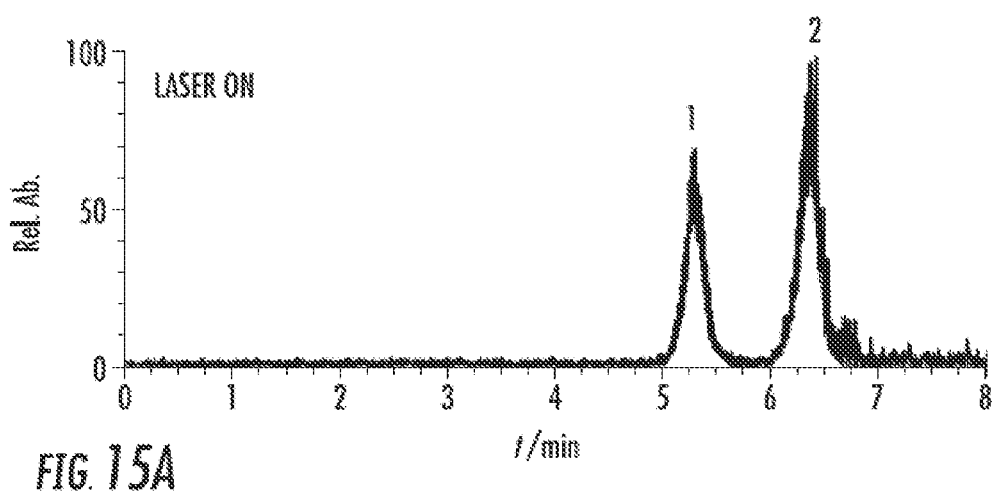
FIGS. 15A & B show (a) relative abundance versus time data for a testing solution containing both rhodamine B (1) and rhodamine 6G (2) that were laser desorbed and separated by HPLC, and (b) relative abundance versus time data for a testing solution where a laser beam was not applied to the specimen.
Figure 15B:
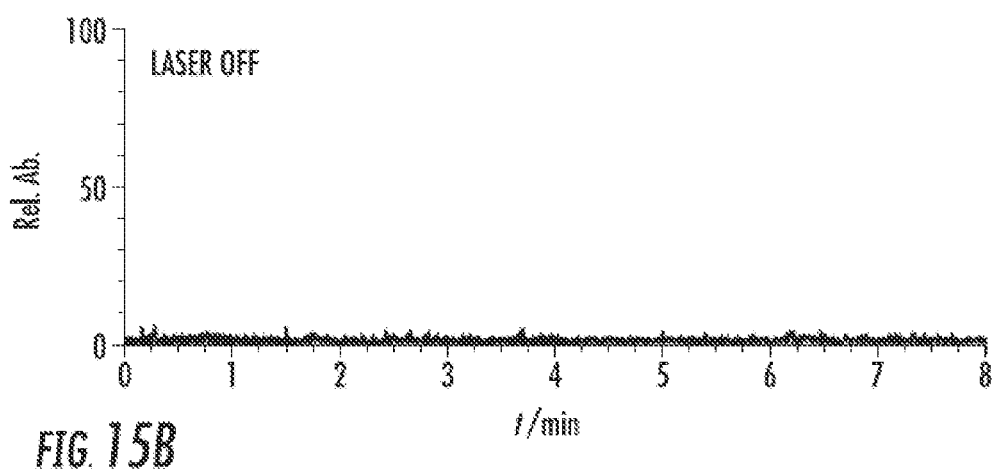

FIG. 15(a) shows the relative intensity versus time data from the mass spectrometer, which demonstrates that the HPLC separated the two rhodamine forms. Peak 1 corresponds to rhodamine B, while Peak 2 corresponds to rhodamine 6G. FIG. 15(b) shows a control where the laser beam was not applied to the target sit. This data clearly demonstrates the efficacy of the laser desorption technique for the small sample size analysis described herein.

Other solvent delivery systems are possible. Laser ablation directly into the solvent is possible. Laser desorption (LD) or ablation (LA) is possible in transmission or reflective geometry, at an acute, right or obtuse angle, directly into a liquid junction at the surface of interest that is formed between a solvent dispensing and retrieving unit and the surface. Analysis of analytes is necessarily limited or specific for material that is not dissolved simply by contact of the solvent to the surface. The laser desorption or laser ablation methods of the invention permit the removal of an otherwise difficult to solubilize analyte. The terms laser ablation and laser desorption will sometimes hereinafter be used interchangeably as the precise mechanism by which the laser causes the analyte to be released from the specimen can vary. A solvent retrieval and extraction system can include a surface sampling probe which creates a wall-less liquid junction, or the invention can utilize a sealing surface sampling probe. The ablated surface material collected in the liquid is available for further processing or direct analysis by one or more techniques including spectroscopic and mass spectrometric methods or others. The analyte can accumulate in the solvent either by dissolving or by suspension. The laser ablation can ablate the analyte into particles of a size that the particles are more susceptible to dissolution or suspension or other methods of extraction. The dispensing and extraction unit can operate as an autonomous droplet dispense/aspirate device or in continuous flow configurations. Analysis of the ablated analyte collected in solution is possible at any point above the ablation region in the liquid junction and along the length of the transport tubing to an end detector or waste. Continuous flow and autonomous dispense configurations also provide for means to collect the ablated analyte for further processing, such as preconcentration, cleanup or material separations, before any analysis. One embodiment of the invention provides for laser ablation into the liquid junction formed using a continuous flow probe, with the effluent from the probe connected to an inductively coupled plasma mass spectrometer (ICP-MS) for elemental determination of the ablated material. With mass spectrometry as a detection system the method might also be used with electrospray ionization (ESI) or atmospheric pressure chemical ionization (APPCI), and possibly other methods if the material ablated from the solvent intractable surface is of the size range and chemical characteristics appropriate to be ionized by these methods and molecular information is desired.

The invention can provide for co-registration of topography, bulk modulus, material stiffness, electrochemical strain, as well as position and chemical signal so multimodal nanoscale imaging is possible. The invention provides a means to acquire analytical data for a fundamental understanding of the spatial distribution of inorganic and organic components in a material surface, such as the spatial distribution of chemical and elemental components in photovoltaic and energy storage devices.

The systems and methods of the invention will provide an alternative to direct LA or LD methods used with ICP optical or mass spectral methods for elemental determinations in normal LA-ICP-MS (or optical detection) ablated particles are transported to the ICP via a high speed gas and transfer tine. Loss of analyte on transport between ablation cell and detection can be eliminated by the invention—100% collection and transfer. Samples are collected into solution and multiple spectroscopic methods can be implemented in serial (maybe parallel) processing for sample characterization. Solid standard samples are unnecessary since calibrate against solutions standards is possible, simplifying quantitation. In some embodiments spatially revolved data preserved so imaging is possible. The present invention provides LA into extremely low volumes (100 nL is possible) resulting in a high concentration of ablated material.

It can be advantageous to limit the size of the laser spot at the sample surface to enhance chemical spatial resolution of the sample. The laser light can be collimated through a restricting aperture of smaller dimension than the wavelength of the light. The laser spot size can also be reduced below the wavelength of the light by using the same effect as exploited in Near Field Optical Microscopy. In this case the laser light impinging on a probe with a nanometer size tip is amplified in intensity but limited to the dimensions of the probe tip.

Figure 16:
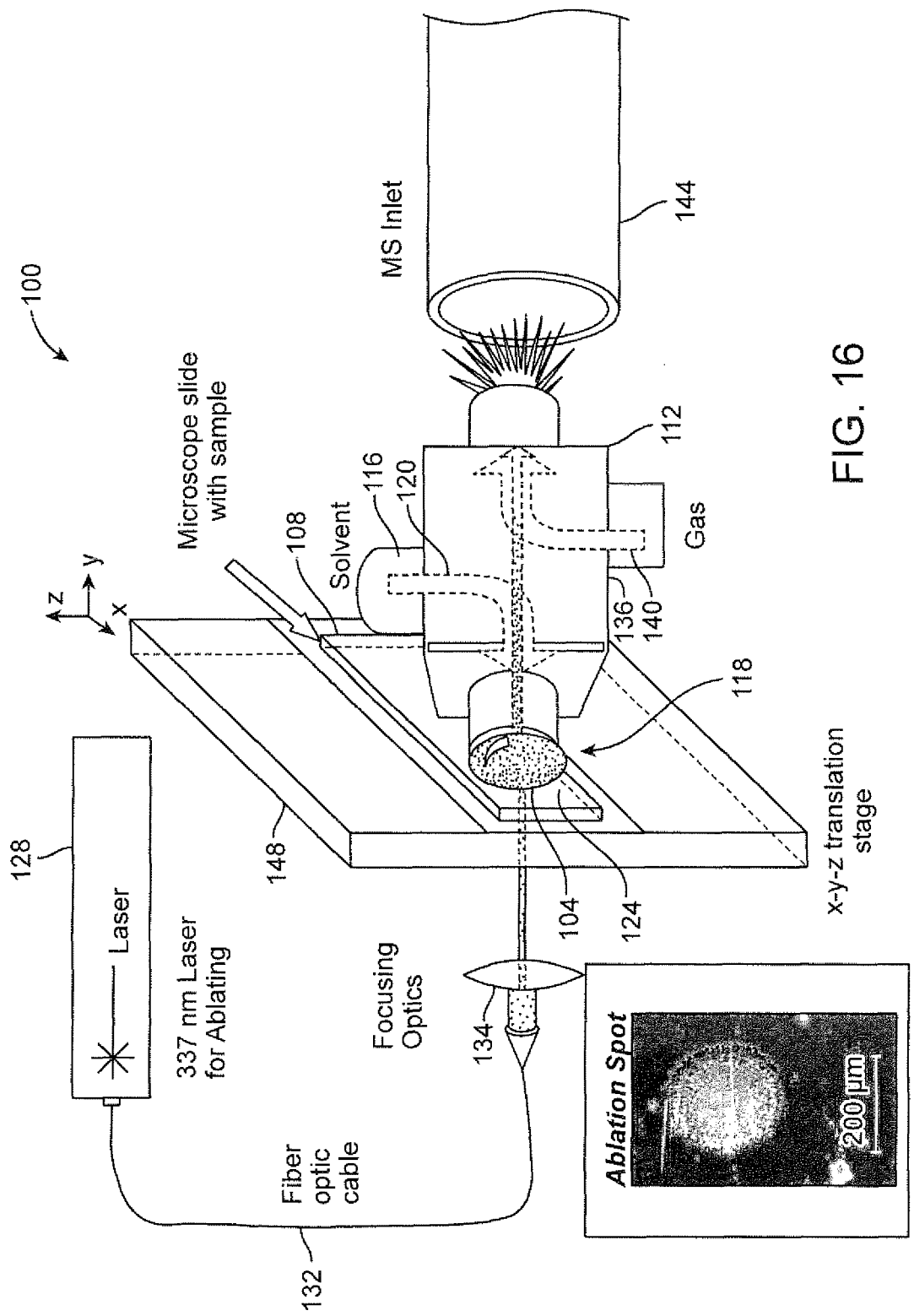
FIG. 16 is a schematic diagram of a laser ablation surface sampling system according to the invention.

There is shown in FIG. 16 a system 100 according to the invention in which a sample 104 is provided on a suitable stage such as slide 108. A surface sampling probe 112 has a solvent inlet 116 which directs solvent to probe tip 118. Solvent 120 flows through the probe 112 to the tip 118 and can form a liquid microjunction 124 between the sample 104 and probe tip 118. A laser source producing a laser beam at a suitable wavelength, such as 337 nm, connects with a fiber optic cable 132 or other structure to direct the beam towards the sample 104. Focusing optics such as tens 134 can be provided. A specimen stage such as x-y-z translation stage 148 can be provided to properly position the sample 104. The stage 148 and slide 108 can be transmissive to the wavelength of laser radiation in the case that the laser beam is directed from a side of the stage 148 that is opposite to the probe 112. The laser beam ablates some of the analyte in the specimen, to a size where it can go into solution in the solvent 124. A gas stream 136 is provided through an inlet 140 to extract the solvent and direct it to the mass spectrometer inlet 144.

There is shown in FIG. 17 a system 150 including a sampling probe 154 which directs a solvent to specimen 160 and forms a liquid microjunction 158 between the probe 154 and the specimen 160. Laser radiation h(γ) 172 can be directed through the probe 154, or a beam 168 can be directed from a side opposite to the probe 154.

There is shown in FIG. 18 a system 180 in which a dispensing probe 186 is provided to dispense solvent to a specimen 198. An extraction conduit 190 can be provided to remove the solvent. The outlet of the dispensing probe 186 and inlet of the extraction conduit 190 can be separated by a distance. A liquid microjunction 194 can be formed by solvent between the dispensing probe 186, sample 198, and possibly also extraction conduit 190. Laser radiation 202 can be provided on the same side of the specimen 198 as the probe 186, or laser radiation 226 can be provided from an opposite side. In either case, the laser radiation ablates the specimen and the analyte causing some of the analyte to go into solution in the solvent.

There is shown in FIG. 19 a system 210 with a surface sampling probe 214 which can have sealing structure 218 at the tip to form a liquid tight seal between the probe 214 and a specimen 222. Laser radiation 224 can be directed through the probe, or the radiation can be directed from a side of the probe if the probe is made of a transmissive material or portion, or the laser radiation 226 can be directed from a side opposite the probe.

Example 4

Laser Ablation into a Liquid Junction Formed with a Surface Using a Microjunction Surface Sampling Probe A transmission geometry setup for LA into a liquid junction formed with a surface using a liquid microjunction surface sampling probe. A red marker (Sharpie) containing rhodamine 6G in the dye solution was applied as a thin film on a glass slide. Using 95%/5/0.1% water/methanol/formic acid as solvent. Rhodamine 6G in such a thin film is not soluble. Laser ablation by a 337 nm laser, 60 μJ/pulse, 10 Hz, 30 s created small particles of the rhodamine 6G that allowed some of the rhodamine to solubilize and be ionized by electrospray ionization.

Figure 20:
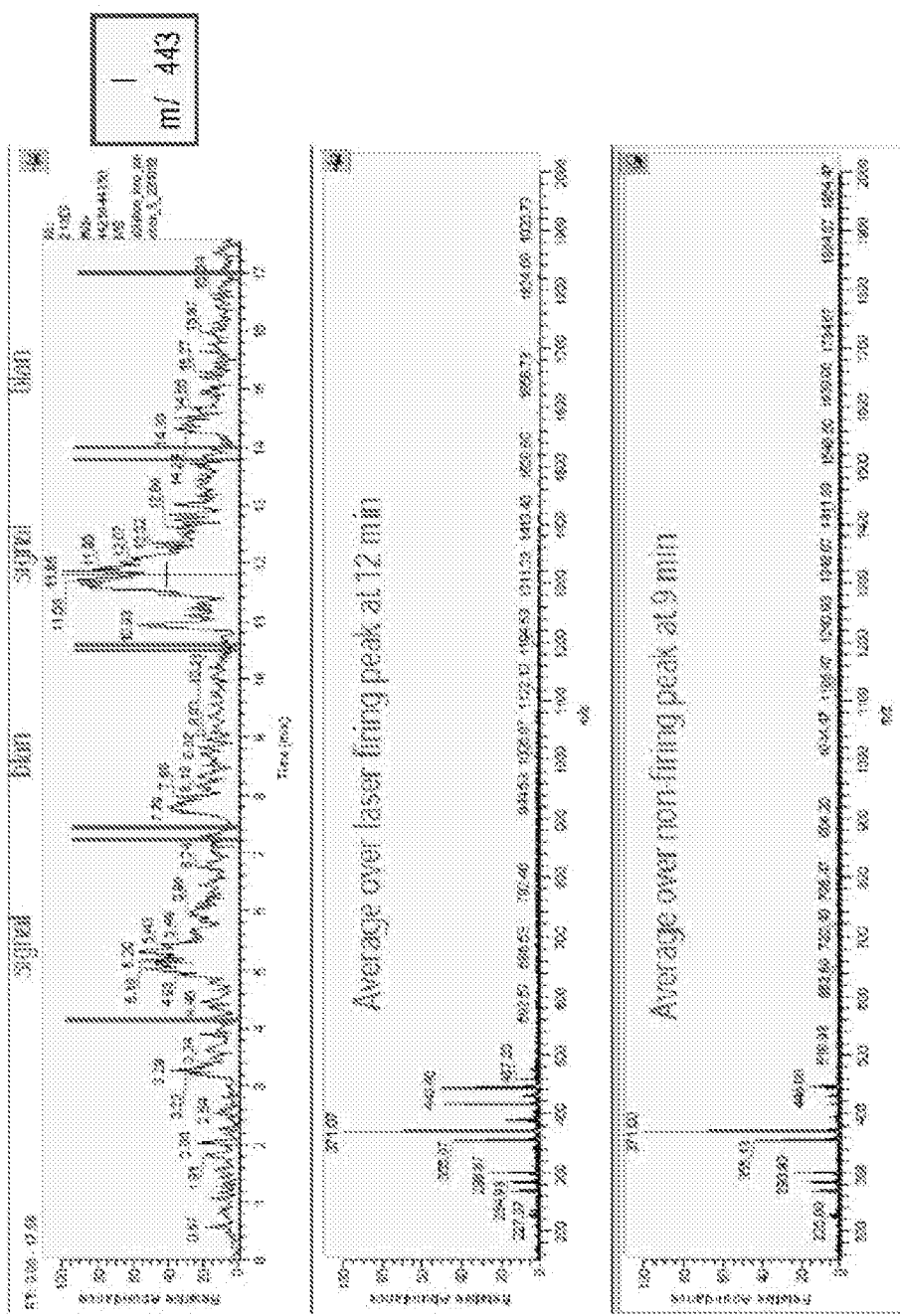
FIG. 20 is a chronogram of the extracted ion current for rhodamine 6G m/z 443 for a defined sequence (Panel 1), the averaged full scan spectrum of the signal peak (Panel 2), and the averaged full scan mass spectrum of the blank peak (Panel 3).

There is shown in Panel 1 of FIG. 20 the chronogram of the extracted ion current for rhodamine 6G, m/z 443 for a sequence of Signal-laser On for 30 s followed by a 2 minute wait to washout the system. The probe was then lifted off the surface and moved to a new sample area where a Blank-laser OFF was preformed for 30 s into a formed liquid microjunction on a rhodamine thin film surface. The surface was a thin film of rhodamine 6G created by applying sharpie marker directly a glass surface. The solvent was 95/5/0.1% water/methanol/formic acid with a flow rate of 10 μL/min. The laser was a 337 nm Nitrogen laser with a 10 Hz repetition rate, operating at 60 µJ/pulse, with a spot size of 200 µm. Panel 2 shows the averaged full scan mass spectrum of the signal peak (Laser ON) at 12 min, showing the presence of the protonated species of rodamine 6G m/z 443. Panel 3 shows the averaged full scan mass spectrum of the blank peak (Laser OFF) at 9 min, showing the absence of the protonated rhodamine 6G m/z 443 peak.

Figure 21:
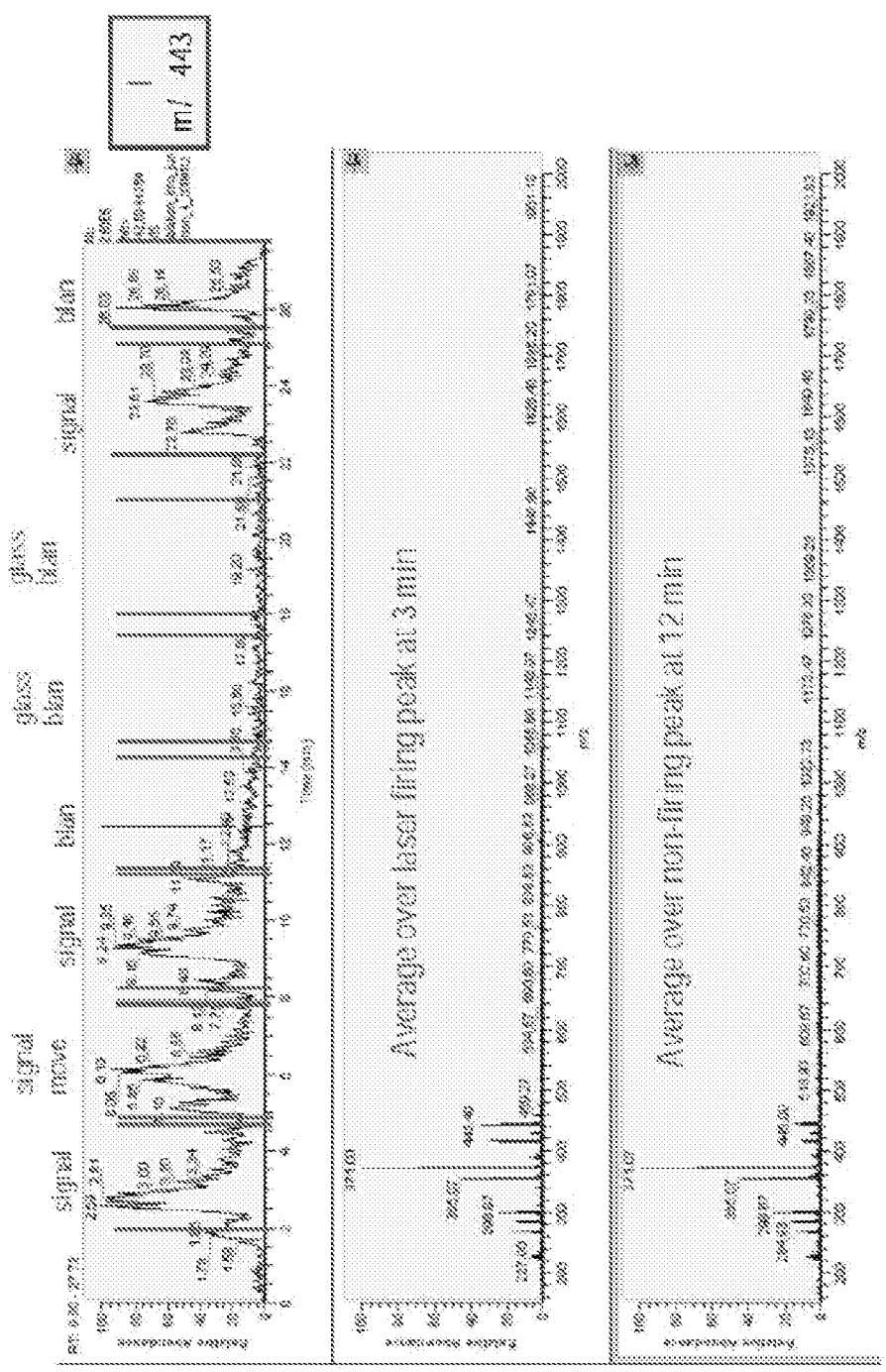
FIG. 21 is the chronogram of the extracted ion current for rhodamine 6G m/z 443 for a defined sequence (Panel 1), the averaged full scan mass spectrum of the signal peak (Panel 2), and the averaged full scan mass spectrum of the blank peak.

There is shown in Panel 1 of FIG. 21 the chronogram of the extracted ion current for rhodamine 6G, m/z 443 for a sequence (Laser ON) for 30 s, with a 2 min washout time followed by a (Laser ON) for 30 s with a 2 min washout time after moving the probe to a new spot without lifting off of the surface, followed by tilling the probe off of the surface to and moving to a new area with a (Laser ON) 30 s and a 2 min washout time, followed by lifting the probe off of the surface to and moving to a new area (Laser OFF) for 30 s with a 2 min washout time, followed by lifting the probe off of the surface and moving to an area without rhodamine on the glass surface with (Laser (OFF) for 30 s with a 2 min washout time, followed by lifting the probe off of the surface and moving to an area without rhodamine on the glass surface with (Laser ON) for 30 s with a 2 min washout time, followed by lifting the probe off of the surface to and moving to a new area with a (Laser ON) 30 s and a 2 min washout time, followed by lifting the probe off of the surface to and moving to a new area (Laser OFF) for 30 s with a 2 min washout time. The surface was a thin film of rhodamine 6G created by applying a sharpie marker directly a glass surface. The solvent was 95/5/0.1% water/methanol/formic acid with a flow rate of 10 µL/min. The laser was a 337 nm Nitrogen laser with a 10 Hz repetition rate, operating at 60 µJ/pulse, with a spot size of 200 µm. Panel 2 shows the averaged full scan mass spectrum of the signal peak (Laser ON) at 3 min, showing the presence of the protonated species of rodamine 6G m/z 443. Panel 3 shows the averaged full scan mass spectrum of the blank peak (Laser OFF) at 12 min, showing the absence of the protonated rhodamine 6G m/z 443 peak.

Figure 22:
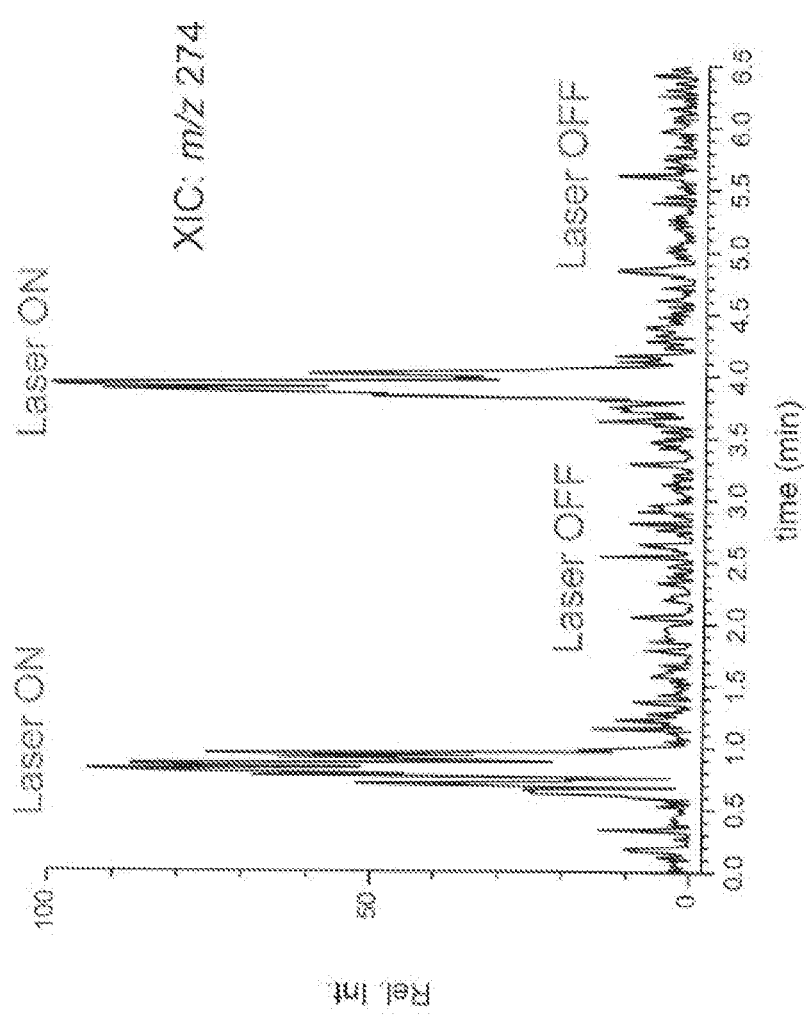
FIG. 22 is a chronogram of the extraction ion current of the trimer of polyaniline m/z 274 for a defined sequence.

FIG. 22 is the chronogram of the extraction ion current of the trimer of polyaniline m/z 274 for a sequence of sequence (Laser ON) for 15 s, with a 2 min washout time followed by a by moving the probe to a new spot without lifting off of the surface with (Laser OFT) for 15 s with a 2 min washout time, followed by moving the probe to a new spot without lifting off of the surface with a (Laser ON) 15 s and a 2 min washout time, followed by a by moving the probe to a new spot without lifting off of the surface with (Laser OFF) for 15 s with a 2 min washout time. The solvent was 80/20/0.1% methanol/water/formic acid with a flow rate of 10 µL/min. The laser was a 337 nm Nitrogen laser with a 10 Hz repetition rate, operating at 60 µJ/pulse, with a spot size of 200 µm. The polyaniline thin film was created electrochemically by cycling 50 times a 1 M HCl solution with 2% aniline.

Figure 23:
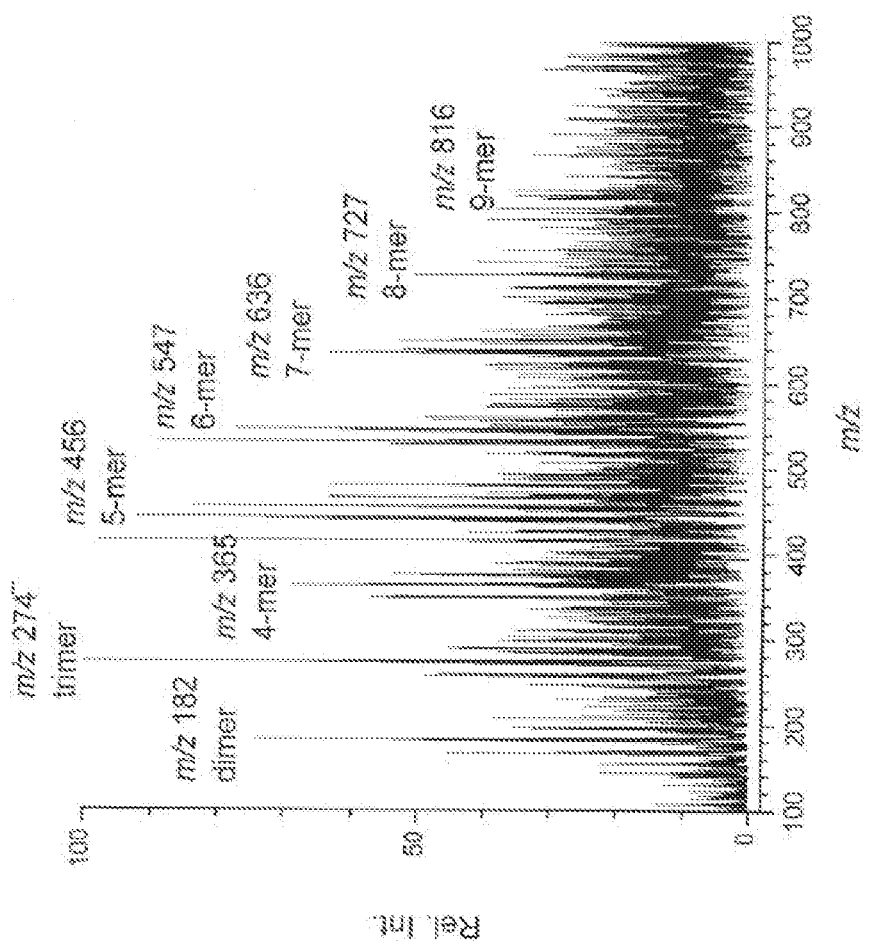
FIG. 23 is the averaged full scan mass spectrum of the signal peak at 0.7 minutes, showing the presence of oligomers of polyaniline from the dimer to the 9-mer.

FIG. 23 is the averaged full scan mass spectrum of the signal peak (Laser ON) at 0.7 min, showing the presence of oligomers of polyaniline from the dimer to the 9-mer. A thin film of polyaniline created electrochemically by cycling 50 times a 1 M HCl solution with 2% aniline. The solvent was 80/20/0.1% methanol/water/formic acid with a flow rate of 10 µL/min. The laser was a 337 nm Nitrogen laser with a 10 Hz repetition rate, operating at 60 µJ/pulse, with a spot size of 200 µm.

Figure 24:
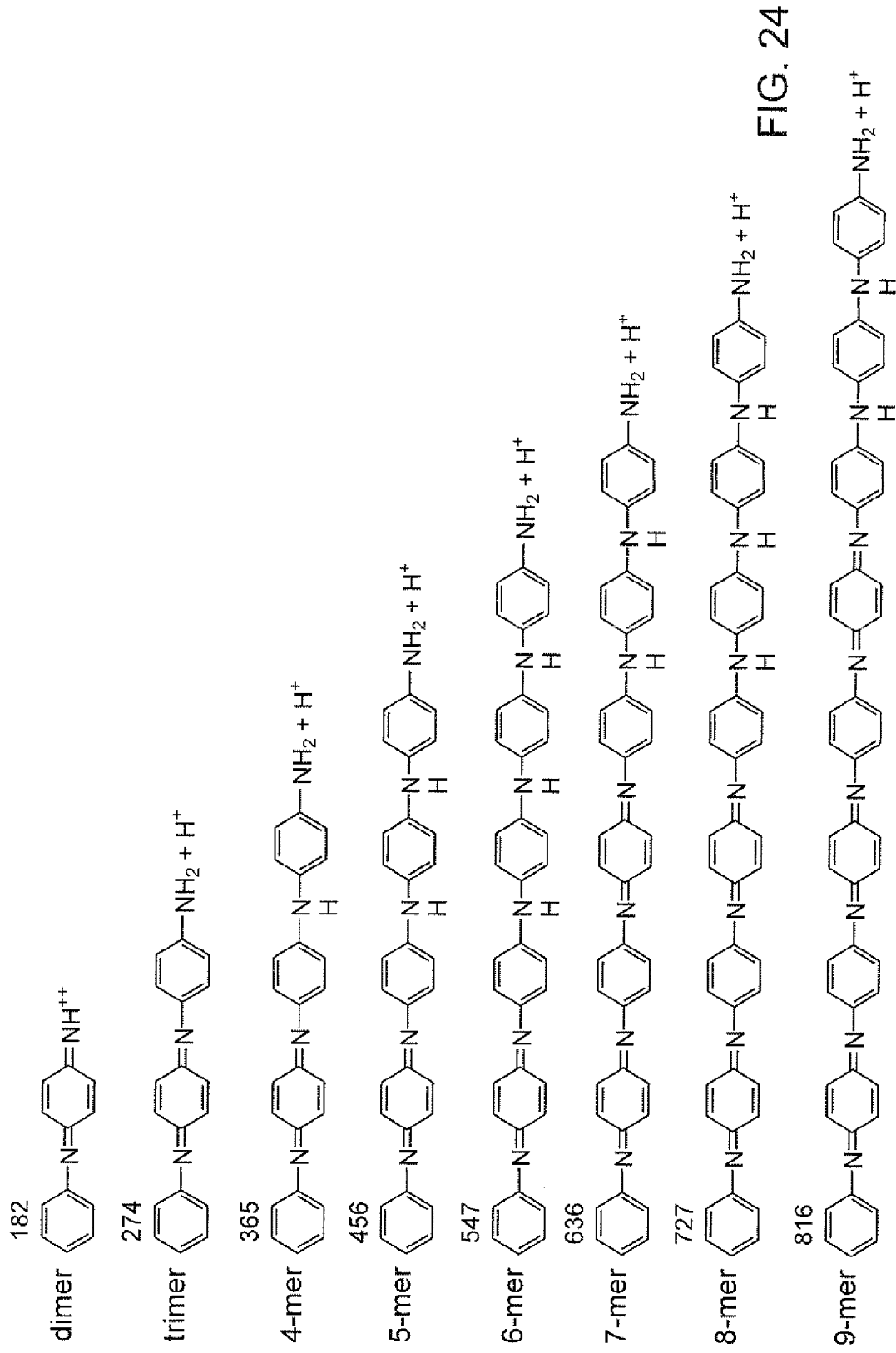
FIG. 24 is a depiction of potential structures of the polyaniline oligomers formed by electrospray.

FIG. 24 depicts the potential structures of the polyaniline oligomers formed by electrospray taken from A. R Dolan, T. D Wood, *Synthetic Metals*, 143, (2004) 243-250, the disclosure of which is hereby incorporated by reference.

Figure 25:
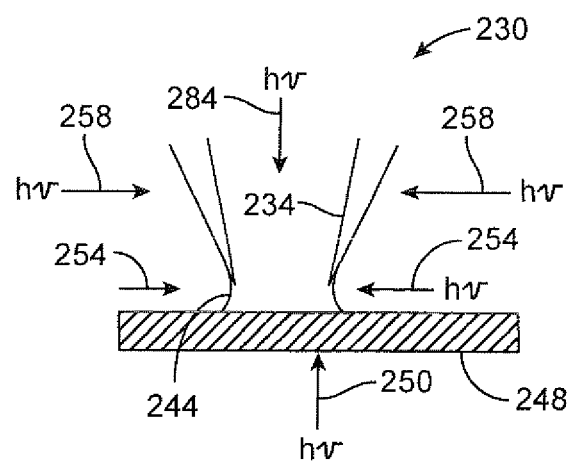
FIG. 25 is a schematic of an embodiment of a laser ablation surface sampling system incorporating atomic force microscopy.

There is shown in FIG. 25 a system 230 in which a sampling probe 234 also is capable of functioning as an atomic force microscopy probe. A solvent can flow through the probe to a specimen 240, and with the specimen 240 can form a liquid microjunction 244. Laser radiation can be directed from one or more angles or directions, such as a beam 248 through the probe 234, beam 250 from a side of the specimen 240 opposite to the probe 234, or beams 254 from the sides of the specimen 240. Beams 258 can be directed through the sides of the probe 234 if the probe is made of a transmissive material. The probe 234 can be constructed according to standard principles and methods for atomic force microscopy, and the data so obtained can be processed by known methods of analysis for atomic force microscopy.

Figure 26:
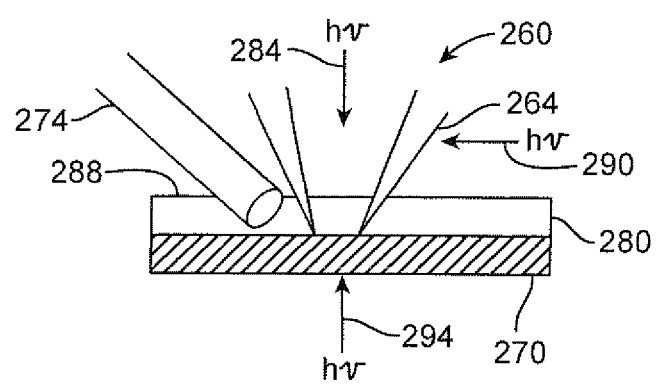
FIG. 26 is and alternative embodiment of a laser ablation surface sampling system incorporating atomic force microscopy.

There is shown in FIG. 26 a system 260 in which a surface sampling probe 264 is also useful as an atomic force microscopy probe. The specimen 280 can be provided on a suitable specimen stage 270. A separate solvent extraction conduit 274 can be provided to remove solvent containing analyte that has entered the solvent after ablation by a laser source. The laser can direct a beam form one or more angles, such as a beam 248 directed through the probe 234, a beam 290 can be transmitted through a side of the probe if the probe material is transmissive, or a beam 294 can be directed from a side of the specimen 280 opposite to the probe 264.

Figure 27A:
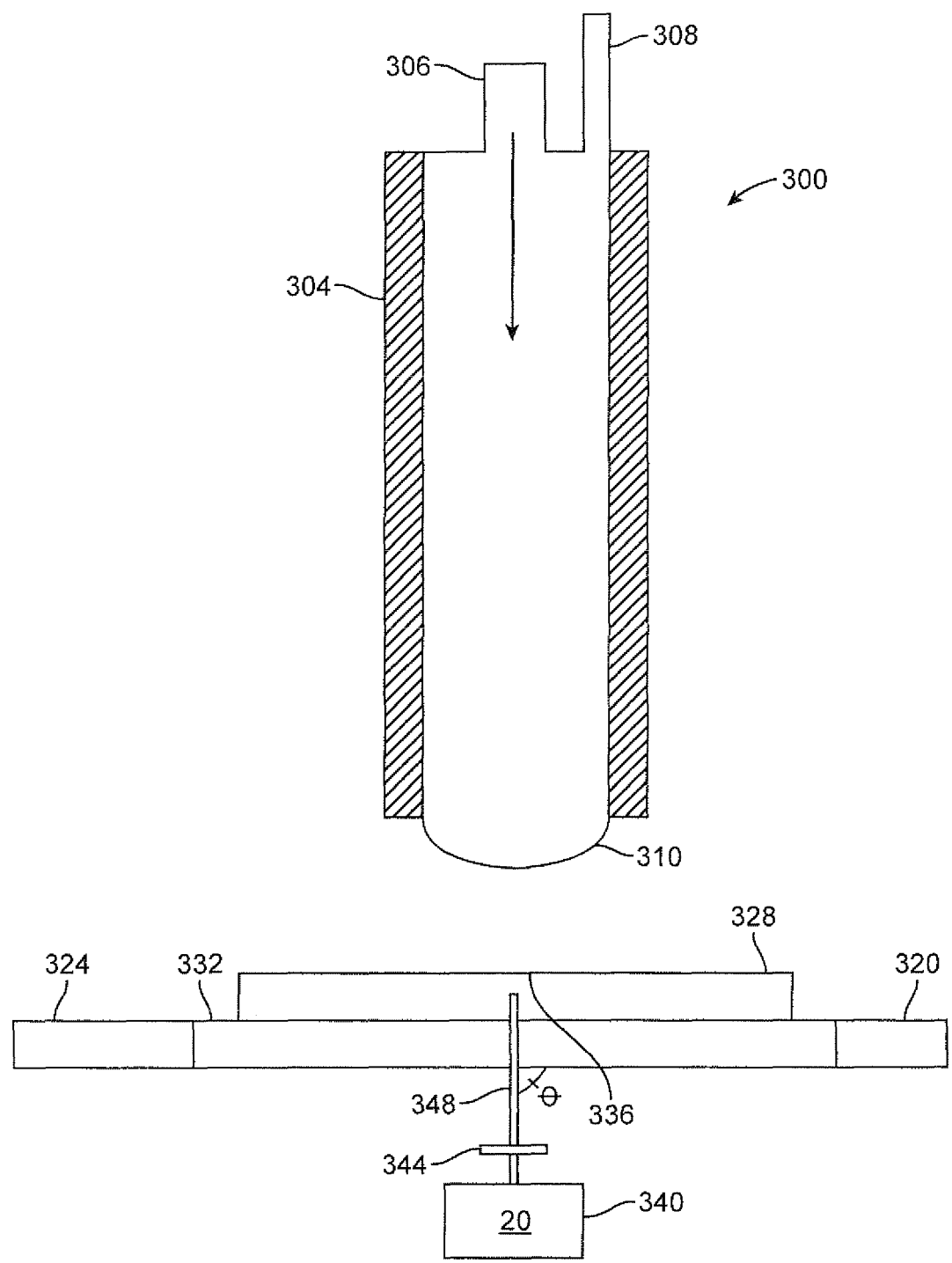
Figure 27B:
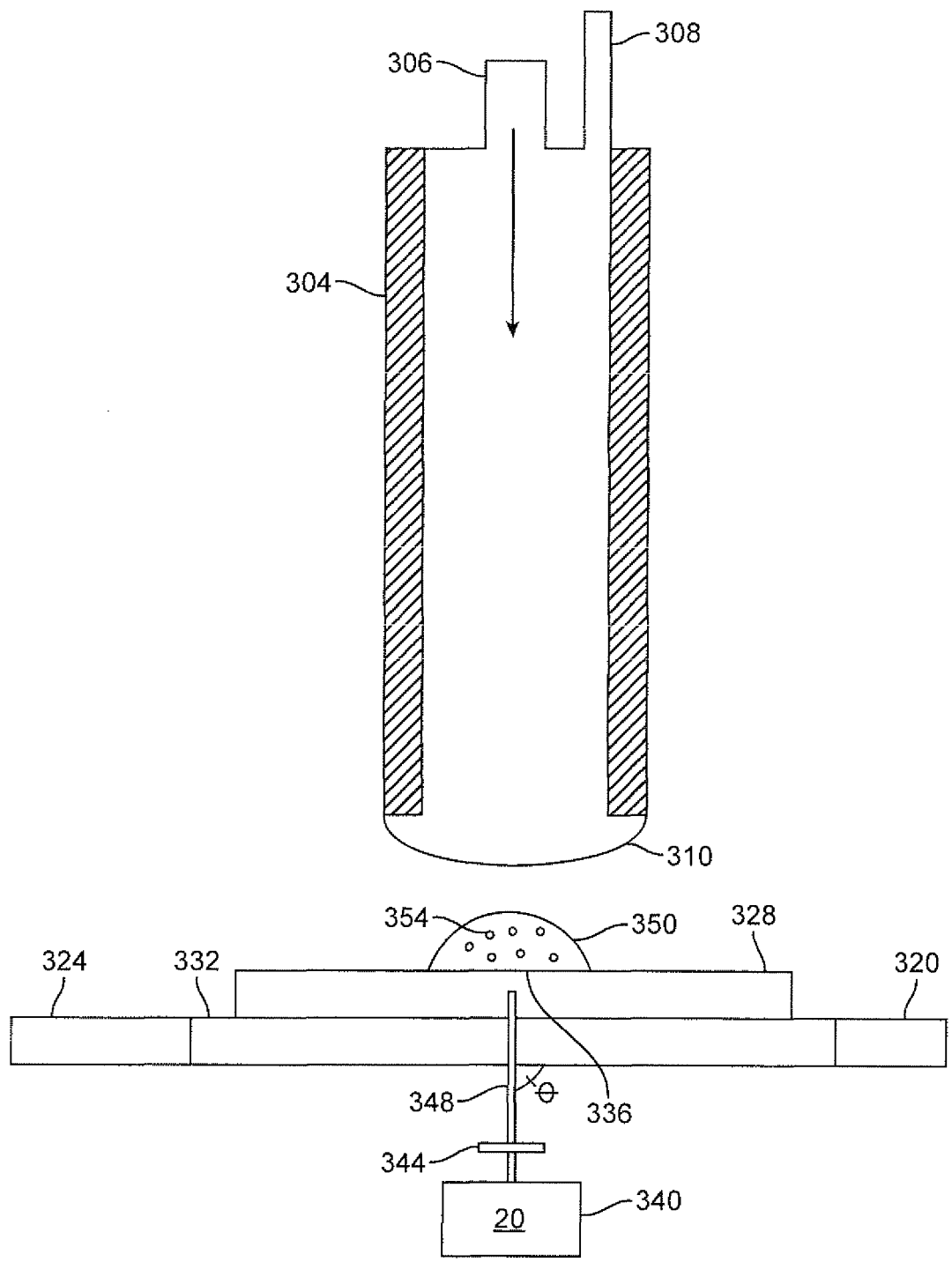

There is shown in FIG. 27A-C a system 300 in which a surface sampling probe 304 has a solvent inlet 306 and a solvent outlet 308. A specimen 328 can be provided on a suitable specimen stage 320. A laser source 340 can be provided to produce a laser beam 348. A suitable optical coupler 344 can be provided. If the laser beam 348 is directed from a source on a side of the stage 320 opposite to the specimen 328, a transmissive region 332 can be provided in the stage 320 with a non-transmissive region 324. Solvent is supplied at a rate so as to form a meniscus 310 (FIG. 27A) and then a drop 350 on a surface 336 of the specimen 328 (FIG. 27B). Ablation by the laser beam 348 creates dissolved or suspended analyte 354. The droplet and analyte can then be extracted as by suctioning into a droplet 358 containing the analyte 354 for further analysis.

One embodiment would be LA into a liquid junction formed between the AFM probe and the surface with the liquid analyzed using an inductively coupled plasma mass spectrometer (ICP-MS) for elemental determination of the ablated material With mass spectrometry as a detection system the method might also be used with electrospray ionization (ESI) or atmospheric pressure chemical ionization (AP-PCI) or other if the material ablated from the solvent intractable surface is of the size range and chemical characteristics appropriate to be ionized by these methods and molecular information is desired.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims.

We claim:

1. A system for performing analysis of at least one analyte present in a solid sample, comprising:
   a laser source for emitting a laser beam toward a specimen on a specimen stage to generate ablated analyte;
   a solvent dispensing and extraction system, the solvent dispensing and extraction system dispensing a solvent adjacent to a surface of the sample such that at least a portion of the ablated analyte can be dissolved in the solvent, wherein the solvent dispensing and extraction system forms a liquid microjunction between the solvent dispensing and extraction system and a surface of the specimen, the laser beam being focused at sample material within the microjunction, where the solvent dispensing and extraction system comprises a sampling probe for dispensing the solvent; and where the laser directs the laser beam through the sampling probe to the specimen;

the solvent dispensing and extraction system having structure for extracting the analyte-containing solvent for analysis.

2. A system for performing analysis of at least one analyte present in a solid sample, comprising:

a laser source for emitting a laser beam toward a specimen on a specimen stage to generate ablated analyte;

a solvent dispensing and extraction system, the solvent dispensing and extraction system dispensing a solvent adjacent to a surface of the sample such that at least a portion of the ablated analyte can be dissolved in the solvent, wherein the solvent dispensing and extraction system forms a liquid microjunction between the solvent dispensing and extraction system and a surface of the specimen, the laser beam being focused at sample material within the microjunction, where the solvent dispensing and extraction system comprises a sampling probe for dispensing the solvent, and the sampling probe is an atomic force microscopy probe, and wherein the laser beam is emitted through the atomic force microscopy probe;

the solvent dispensing and extraction system having structure for extracting the analyte-containing solvent for analysis.

\* \* \* \* \*